US009175091B2

(12) United States Patent
Kitazawa et al.

(10) Patent No.: US 9,175,091 B2
(45) Date of Patent: Nov. 3, 2015

(54) MONOCLONAL ANTIBODY CAPABLE OF BINDING TO ANEXELEKTO, AND USE THEREOF

(75) Inventors: Takehisa Kitazawa, Shizuoka (JP); Tsukasa Suzuki, Shizuoka (JP); Shigehisa Nagahashi, Kanagawa (JP); Hajime Miyamoto, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 203 days.

(21) Appl. No.: 12/742,947

(22) PCT Filed: Nov. 14, 2008

(86) PCT No.: PCT/JP2008/070739
§ 371 (c)(1),
(2), (4) Date: Oct. 1, 2010

(87) PCT Pub. No.: WO2009/063965
PCT Pub. Date: May 22, 2009

(65) Prior Publication Data
US 2011/0044984 A1 Feb. 24, 2011

(30) Foreign Application Priority Data

Nov. 15, 2007 (JP) ................................. 2007-297168

(51) Int. Cl.
C07K 16/00 (2006.01)
C07K 16/32 (2006.01)
C07K 16/40 (2006.01)
A61K 39/00 (2006.01)

(52) U.S. Cl.
CPC .................. *C07K 16/32* (2013.01); *C07K 16/40* (2013.01); *A01K 2267/0331* (2013.01); *A61K 2039/505* (2013.01); *C07K 2316/96* (2013.01); *C07K 2317/56* (2013.01); *C07K 2317/565* (2013.01); *C07K 2319/30* (2013.01)

(58) Field of Classification Search
CPC ...................................................... C07K 16/00
See application file for complete search history.

(56) References Cited

U.S. PATENT DOCUMENTS

| 5,468,634 | A | * | 11/1995 | Liu ................................. 435/348 |
| 5,709,858 | A | | 1/1998 | Godowski et al. |
| 5,891,996 | A | * | 4/1999 | Mateo de Acosta del Rio et al. ........................... 530/387.3 |
| 2003/0114398 | A1 | * | 6/2003 | Chatterjee et al. .............. 514/42 |
| 2005/0084906 | A1 | * | 4/2005 | Goetsch et al. ................ 435/7.1 |
| 2006/0019340 | A1 | * | 1/2006 | Naor et al. .................... 435/69.1 |
| 2007/0178102 | A1 | | 8/2007 | Yarden et al. |
| 2007/0224174 | A1 | * | 9/2007 | Kang et al. .................... 424/93.7 |
| 2012/0121587 | A1 | | 5/2012 | Maeda et al. |

FOREIGN PATENT DOCUMENTS

| EP | 1 382 969 | 1/2004 |
| JP | 2005-532805 | 11/2005 |
| WO | WO 03/057881 | 7/2003 |
| WO | W02004008147 A2 | 1/2004 |
| WO | W02004039955 A2 | 5/2004 |
| WO | W02007030680 A2 | 3/2007 |
| WO | WO 2007/089871 | 8/2007 |
| WO | WO 2007/114319 | 10/2007 |
| WO | W02008098139 A2 | 8/2008 |
| WO | WO 2009/041643 | 4/2009 |
| WO | WO 2009/062690 | 5/2009 |
| WO | WO 2009/063965 | 5/2009 |

OTHER PUBLICATIONS

Lay et al, Cancer Res 67:3878-3887, 2007.*
O'Bryan et al, Mole and Cell Bio 11:5016-5031, 1991 (IDS filed Jan. 11, 2010, item 25).*
Pascalis et al, The Journal of Immunology vol. 169, 3076-3084, 2002.*
Casset et al, BBRC 307, 198-205 2003.*
Rudikoff et al, Proc. Natl. Acad. Sci. USA 1982 vol. 79: p. 1979.*
Paul, Fundamental Immunology, 3rd Edition, 1993, pp. 292-295.*
Allen et al., "Novel mechanism for gonadotropin-releasing hormone neuronal migration involving Gas6/Ark signaling to p38 mitogen-activated protein kinase," Mol. Cell Biol., 22:599-613 (2002).
Bellosta et al., "Signaling through the ARK tyrosine kinase receptor protects from apoptosis in the absence of growth stimulation," Oncogene., 15:2387-97 (1997).
Budagian et al., "A promiscuous liaison between IL-15 receptor and Axl receptor tyrosine kinase in cell death control," EMBO J., 24:4260-70 (2005).
Chung et al., "Expression of the proto-oncogene Axl in renal cell carcinoma," DNA Cell Biol., 22:533-540 (2003).
Craven et al., "Receptor tyrosine kinases expressed in metastatic colon cancer," Int. J. Cancer, 60:791-797 (1995).
Fridell et al., "GAS6 induces Axl-mediated chemotaxis of vascular smooth muscle cells," J. Biol. Chem., 273:7123-26 (1998).
Gallicchio et al., "Inhibition of vascular endothelial growth factor receptor 2-mediated endothelial cell activation by Axl tyrosine kinase receptor," Blood, 105:1970-76 (2005) (Epub 2004).
Goruppi et al., "Requirement of phosphatidylinositol 3-kinase-dependent pathway and Src for Gas6-Axl mitogenic and survival activities in NIH 3T3 fibroblasts," Mol. Cell Biol., 17:4442-53 (1997).
Hafizi et al., "Interaction of Axl receptor tyrosine kinase with C1-TEN, a novel C1 domain-containing protein with homology to tensin," Biochem. Biophys. Res. Commun., 299:793-800 (2002).

(Continued)

*Primary Examiner* — Lei Yao
(74) *Attorney, Agent, or Firm* — Fish & Richardson P.C.

(57) ABSTRACT

The present inventors have succeeded in producing anti-AXL antibodies with specific functions. The present inventors also discovered that the antibodies have an angiogenesis-suppressive effect and an antitumor effect, and thereby completed the present invention. The anti-AXL antibodies of the present invention are useful as angiogenesis inhibitors and agents for inducing or inhibiting phosphorylation activity.

7 Claims, 12 Drawing Sheets

(56) References Cited

OTHER PUBLICATIONS

Hafizi et al., "Gas6 and protein S. Vitamin K-dependent ligands for the Axl receptor tyrosine kinase subfamily," FEBS J., 273:5231-44 (2006).
Hafizi et al., "Signalling and functional diversity within the Axl subfamily of receptor tyrosine kinases," Cytokine Growth Factor Rev., 17:295-304 (2006).
Holland et al., "Multiple roles for the receptor tyrosine kinase axl in tumor formation," Cancer Res., 65:9294-9303 (2005).
Ito et al., "Expression of receptor-type tyrosine kinase, Axl, and its ligand, Gas6, in pediatric thyroid carcinomas around Chernobyl," Thyroid, 12:971-975 (2002).
Janssen et al., "A novel putative tyrosine kinase receptor with oncogenic potential," Oncogene, 6:2113-20 (1991).
Lay et al., "Sulfasalazine suppresses drug resistance and invasiveness of lung adenocarcinoma cells expressing AXL," Cancer Res., 67:3878-87 (2007).
Linger et al., "TAM receptor tyrosine kinases: biologic functions, signaling, and potential therapeutic targeting in human cancer," Adv. Cancer Res., 100:35-83 (2008).
Liu et al., "Transforming genes in chronic myelogenous leukemia," Proc. Natl. Acad. Sci. USA, 85:1952-56 (1988).
McCloskey et al., "GAS6 mediates adhesion of cells expressing the receptor tyrosine kinase Axl," J. Biol. Chem., 272:23285-91 (1997).
Meric et al., "Expression profile of tyrosine kinases in breast cancer," Clin. Cancer Res., 8:361-367 (2002).
Nakano et al., "Vascular smooth muscle cell-derived, Gla-containing growth-potentiating factor for Ca(2+)-mobilizing growth factors," J. Biol. Chem., 270:5702-05 (1995).
Nakano et al., "Prevention of growth arrest-induced cell death of vascular smooth muscle cells by a product of growth arrest-specific gene, gas6," FEBS Lett., 387:78-80 (1996).
Nakano et al., "Biological properties and gene expression associated with metastatic potential of human osteosarcoma," Clin. Exp. Metastasis, 20:665-674 (2003).
Nemoto et al., Overexpression of protein tyrosine kinases in human esophageal cancer, Pathobiology, 65:195-203 (1997).
Neubauer et al., "Expression of axl, a transforming receptor tyrosine kinase, in normal and malignant hematopoiesis," Blood., 84:1931-41 (1994).
O'Bryan et al., "axl, a transforming gene isolated from primary human myeloid leukemia cells, encodes a novel receptor tyrosine kinase," Mol. Cell Biol., 11:5016-31 (1991).
Pavlaki et al., "Matrix metalloproteinase inhibitors (MMPIs): the beginning of phase I or the termination of phase III clinical trials," Cancer Metastasis Rev., 22:177-203 (2003).
Sainaghi et al., "Gas6 induces proliferation in prostate carcinoma cell lines expressing the Axl receptor," J. Cell Physiol., 204:36-44 (2005).
Sawabu et al., "Growth arrest-specific gene 6 and Axl signaling enhances gastric cancer cell survival via Akt pathway," Mol. Carcinog., 46:155-164 (2007).
Shieh et al., "Expression of axl in lung adenocarcinoma and correlation with tumor progression," Neoplasia, 7:1058-64 (2005).
Stenhoff et al., "Vitamin K-dependent Gas6 activates ERK kinase and stimulates growth of cardiac fibroblasts," Biochem. Biophys. Res. Commun., 319:871-878 (2004).
Sun et al., "Clinical implications of coexpression of growth arrest-specific gene 6 and receptor tyrosine kinases Axl and Sky in human uterine leiomyoma," Mol. Hum. Reprod., 9:701-707 (2003).
Sun et al., "Coexpression of growth arrest-specific gene 6 and receptor tyrosine kinases Axl and Sky in human uterine endometrial cancers," Ann. Oncol., 14:898-906 (2003).
Sun et al., "Coexpression of Gas6/Axl in human ovarian cancers," Oncology, 66:450-457 (2004).
Yamagata et al., "Synaptic adhesion molecules," Curr. Opin. Cell Biol., 15:621-632 (2003).
Vajkoczy et al., "Dominant-negative inhibition of the Axl receptor tyrosine kinase suppresses brain tumor cell growth and invasion and prolongs survival," Proc. Natl. Acad. Sci. USA, 103:5799-5804 (2006).

Varnum et al., "Axl receptor tyrosine kinase stimulated by the vitamin K-dependent protein encoded by growth-arrest-specific gene 6," Nature, 373:623-626 (1995).
Wu et al., "Clinical significance of AXL kinase family in gastric cancer," Anticancer Res., 22(2B):1071-78 (2002).
Zhang et al., "AXL is a potential target for therapeutic intervention in breast cancer progression," Cancer Res., 68:1905-15 (2008).
International Preliminary Report on Patentability for App. Ser. No. PCT/JP2008/070739, dated Jun. 29, 2010, 7 pages.
International Search Report for for App. Ser. No. PCT/JP2008/070739, mailed Dec. 16, 2008, 8 pages.
Berzofsky et al., "Immunogenicity and Antigen Structure," *Fundamental Immunology*, by Paul et al. ($3^{rd}$ Edition), Raven Press (1984), Chapter 21, pp. 58-59 (with English translation).
Li et al., "Axl as a potential therapeutic target in cancer: role of Axl in tumor growth, metastasis and angiogenesis," *Oncogene*, 28(39):3442-3455 (2009).
Roitt et al., *Immunology*, M. Mir, p. 110 (2000) (with English translation).
Rudikoff et al., "Single amino acid substitution altering antigen-binding specificity," *Proc. Natl. Acad. Sci. U.S.A.*, 79(6):1979-1983 (1982).
Berzofsky et. al., "Antigen-antibody interaction," *Fundamental Immunology*, by Paul et al. ($3^{rd}$ Edition), Raven Press ( 1987-1989), Chapter 23, pp. 47-49 (with English translation).
Roitt et al., *Immunology*, M. Mir, 150-155 (2000) (with corresponding English text: Roitt et al., "Antigen Recognition," *Immunology*, $5^{th}$ Edition, 107-112).
Fish & Richardson P.C., Response to Restriction Requirement dated Dec. 18, 2012 in U.S. Appl. No. 13/320,317, filed Jan. 18, 2013, 3 pages.
Altar et al., "AXL receptor tyrosine kinase expression in human breast cancer," Breast Cancer Research and Treatment, Springer, New York, NY (Abstracts—Poster session III) 46(1):91 (1997).
Brown et al., "Tolerance of single, but not multiple, amino acid replacements in antibody VH CDR 2: a means of minimizing B cell wastage from somatic hypermutation?," *J. Immunol.*, 156(9):3285-91 (1996).
Chirino et al., "Minimizing the immunogenicity of protein therapeutics," *Drug Discov. Today*, 9(2):82-90 (2004).
Davies et al., "Affinity improvement of single antibody VH domains: residues in all three hypervariable regions affect antigen binding," *Immunotechnology*, 2(3):169-79 (1996).
Ewert et al., "Stability improvement of antibodies for extracellular and intracellular applications: CDR grafting to stable frameworks and structure-based framework engineering," *Methods.*, 34(2):184-99 (2004).
Giusti et al., "Somatic diversification of S107 from an antiphosphocholine to an anti-DNA autoantibody is due to a single base change in its heavy chain variable region," *Proc. Natl. Acad. Sci. U.S.A.*, 84(9):2926-30 (1987).
Hanes et al., "Picomolar affinity antibodies from a fully synthetic naive library selected and evolved by ribosome display," *Nat. Biotechnol.*, 18(12):1287-92 (2000).
Holt et al., "Domain antibodies: proteins for therapy," *Trends Biotechnol.*, 21(11):484-90 (2003).
Kussie et al., "A single engineered amino acid substitution changes antibody fine specificity," *J. Immunol.*, 152(1):146-52 (1994).
Liu et al., "Fine mapping of the antigen-antibody interaction of scFv215, a recombinant antibody inhibiting RNA polymerase II from *Drosophila melanogaster*," *J. Mol. Recognit.* , 12(2):103-11 (1999).
Maynard et al., "Antibody engineering," *Annu. Rev. Biomed. Eng.*, 2:339-76 (2000).
Pardridge et al., "Enhanced endocytosis in cultured human breast carcinoma cells and in vivo biodistribution in rats of a humanized monoclonal antibody after cationization of the protein," *J. Pharmacol. Exp. Ther.*, 286(1):548-54 (1998).
Pini et al., "Design and use of a phage display library. Human antibodies with subnanomolar affinity against a marker of angiogenesis eluted from a two-dimensional gel," *J. Biol. Chem.*, 273(34):21769-76 (1998).

(56) References Cited

OTHER PUBLICATIONS

R&D Systems, Safety Data Sheet, "Human Axl Antibody Monoclonal Mouse 1gG1 Clone # 108724," Catalog No. MAB154 (2012).
Schildbach et al., "Contribution of a single heavy chain residue to specificity of an anti-digoxin monoclonal antibody," *Protein Sci.*, 3(5):737-49 (1994).
Schildbach et al., "Heavy chain position 50 is a determinant of affinity and specificity for the anti-digoxin antibody 26-10," *J. Biol. Chem.*, 268(29):21739-47 (1993).
Vaisitti et al., "Cationization of monoclonal antibodies: another step towards the "magic bullet"?," *J. Biol. Regul. Homeost. Agents.*, 19(3-4):105-12 (2005).
Vajdos et al., "Comprehensive functional maps of the antigen-binding site of an anti-ErbB2 antibody obtained with shotgun scanning mutagenesis," *J. Mol. Biol.*, 320(2):415-28 (2002).
Xiang et al., "Study of B72.3 combining sites by molecular modeling and site-directed mutagenesis," *Protein Eng.*, 13(5):339-44 (2000).
Yamagata et al., "Synaptic adhesion molecules," *Curr. Opin. Cell Biol.*, 15(5):621-32 (2003).
USPTO Restriction Requirement in U.S. Appl. No. 13/320,317, dated Dec. 18, 2012, 13 pages.
International Preliminary Report on Patentability for App. Ser. No. PCT/JP2010/058166, dated Dec. 16, 2011, 15 pages.
Fish & Richardson P.C., Reply to Office Action dated Apr. 25, 2013 in U.S. Appl. No. 13/320,317, filed Oct. 25, 2013, 26 pages.
Gussow et al., "Humanization of monoclonal antibodies," *Methods Enzymol.*, 203:99-121 (1991).
Mariuzza et al., "The structural basis of antigen-antibody recognition," *Annu. Rev. Biophys. Chem.*, 16:139-59 (1987).
Paul, Fundamental Immunology, Third Edition, M. Mir, 3:250 (1987-1988) (with English translation of relevant page).
Tarantula, "Glossary of biomedical terms", M: Inform Its Rospatent, 126 (2005) (with English translation of relevant page, see p. 105).
Winkler et al., "Changing the antigen binding specificity by single point mutations of an anti-p24 (HIV-1) antibody," *J. Immunol.*, 165:4505-14 (2000).
USPTO Non-Final Office Action in U.S. Appl. No. 13/320,317, dated Apr. 25, 2013, 24 pages.
USPTO Final Office Action in U.S. Appl. No. 13/320,317, dated Jan. 15, 2014, 17 pages.
Paul, "Immunology," a Russian translation of English book, M.: Mir, 3:248-251 (1987-1988) (with English bibliographic data).
Pokrovskiy, "Small medical encyclopedia," in 6 volumes. Meditsinskaya entsiclopedia, 1A:139, right column (1991) (with English bibliographic data).
Stepanov, "Molecular Biology. Structure and Functions of Proteins," Nauka, 144-145 (2005) (with English bibliographic data).
Yarilin, Fundamentals of Immunology, Meditsina, 203-204 (1999) (with English bibliographic data).
Fish & Richardson P.C., Reply to Office Action dated Jan. 15, 2014 in U.S. Appl. No. 13/320,317, filed Apr. 9, 2014, 21 pages.
USPTO Non-Final Office Action in U.S. Appl. No. 13/320,317, dated Apr. 8, 2015, 6 pages.
Vajkoczy et al., "Dominant-negative inhibition of the Axl receptor tyrosine kinase suppresses brain tumor cell growth and invasion and prolongs survival—Date Supplement" Apr. 11, 2006;103(15):5799, p. 1S. Retrieved from the Internet: http://www.ncbi.nlm.nih.gov/pmc/articles/PMC1458653/bin/pnas_0510923103_index.html [retrieved on Feb. 10, 2015].

* cited by examiner

| Clone# | Subtype | Anti-tumor activity (Panc-1: 2nd trial) | Binding domain | Inhibition of ligand-induced AXL phosphorylation |
|---|---|---|---|---|
| #225 | 1 | ++ | FND-1 | − |
| #284 | 2a | ++ | FND-1, IgD2 | − |
| #7 | 1 | + | IgD2 | + |
| #51 | 1 | + | IgD2 | + |
| #285 | 2a | − | IgD2 | − |
| #223 | 2b | − | IgD2 | − |
| #96 | 1 | − | IgD1 | − |
| #292 | 2b | − | IgD2 | − |
| #258 | 1 | − | IgD2 | − |

−: TGI(%) <30, +: TGI(%) <60, ++: 60=<TGI(%)

FIG. 6

SEQUENCE LISTING

<160> NUMBER OF SEQ ID NOS: 10

<210> SEQ ID NO 1
<211> LENGTH: 21
<212> TYPE: DNA
<213> ORGANISM: Artificial
<220> FEATURE:
<223> OTHER INFORMATION: An artificially synthesized primer sequence

```
<400> SEQUENCE: 1
gggccagtgg atagacagat g                                               21

<210> SEQ ID NO 2
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 2
gctcactgga tggtgggaag atg                                             23

<210> SEQ ID NO 3
<211> LENGTH: 138
<212> TYPE: PRT
<213> ORGANISM: Artificial
<220> FEATURE:
<223> OTHER INFORMATION: An artificially synthesized peptide sequence

<400> SEQUENCE: 3

Met Ala Val Leu Val Leu Leu Phe Cys Leu Val Thr Phe Pro Ser Cys
1               5                   10                  15

Ile Leu Ser Gln Val Gln Leu Lys Gln Ser Gly Pro Gly Leu Val Ala
            20                  25                  30

Pro Ser Gln Ser Leu Ser Ile Thr Cys Thr Val Ser Gly Leu Ser Leu
        35                  40                  45

Thr Ser Phe Gly Val Asp Trp Val Arg Gln Ser Pro Gly Lys Gly Leu
    50                  55                  60

Glu Trp Leu Gly Val Ile Trp Gly Gly Gly Ser Thr Asn Tyr Asn Ser
65                  70                  75                  80

Ala Leu Lys Ser Arg Leu Ser Ile Ser Lys Asp Asn Ser Lys Ser Gln
                85                  90                  95

Val Phe Leu Lys Met Asn Ser Leu Gln Thr Asp Asp Thr Ala Met Tyr
            100                 105                 110

Tyr Cys Ala Gly Glu Gly Ser Lys Tyr Gly Ala Trp Phe Ala Tyr Trp
        115                 120                 125

Gly Gln Gly Thr Leu Val Thr Val Ser Ser
    130                 135

<210> SEQ ID NO 4
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 4

Ser Phe Gly Val Asp
1               5

<210> SEQ ID NO 5
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 5

Val Ile Trp Gly Gly Gly Ser Thr Asn Tyr Asn Ser Ala Leu Lys Ser
1               5                   10                  15
```

```
<210> SEQ ID NO 6
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 6

Glu Gly Ser Lys Tyr Gly Ala Trp Phe Ala Tyr
1               5                   10

<210> SEQ ID NO 7
<211> LENGTH: 131
<212> TYPE: PRT
<213> ORGANISM: Artificial
<220> FEATURE:
<223> OTHER INFORMATION: An artificially synthesized peptide sequence

<400> SEQUENCE: 7

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Asn Ile
        35                  40                  45

Val His Thr Asn Gly Asn Thr Tyr Leu Glu Trp Tyr Leu Gln Lys Pro
    50                  55                  60

Gly Gln Ser Pro Glu Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Ile Pro Phe Thr Phe Gly Thr Gly Thr Lys Leu
        115                 120                 125

Glu Ile Lys
    130

<210> SEQ ID NO 8
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 8

Arg Ser Ser Gln Asn Ile Val His Thr Asn Gly Asn Thr Tyr Leu Glu
1               5                   10                  15

<210> SEQ ID NO 9
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 9

Lys Val Ser Asn Arg Phe Ser
1               5

<210> SEQ ID NO 10
```

```
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 10

Phe Gln Gly Ser His Ile Pro Phe Thr
1               5
```

MONOCLONAL ANTIBODY CAPABLE OF BINDING TO ANEXELEKTO, AND USE THEREOF

CROSS-REFERENCE TO RELATED APPLICATIONS

This application is the National Stage of International Application Serial No. PCT/JP2008/070739, filed on Nov. 14, 2008, which claims the benefit of Japanese Application Serial No. 2007-297168, filed on Nov. 15, 2007. The contents of the foregoing applications are incorporated herein by reference.

TECHNICAL FIELD

The present invention relates to monoclonal antibodies that bind to anexelekto, agents containing the antibodies as an active ingredient, and methods for using the antibodies.

BACKGROUND

Anexelekto (also referred to as "AXL", "UFO", "ARK", or "TYRO7"; hereinafter referred to as "AXL"), which has been cloned from patients with chronic myeloid leukemia, is an oncogene capable of transforming mouse NIH3T3 cells when highly expressed (Non-patent Documents 1 and 2). AXL protein is a 140-kDa receptor tyrosine kinase (Non-patent Document 3), and is said to be responsible for signal transduction to downstream molecules through its autophosphorylation, which occurs after it binds to the ligand Gas6 (growth arrest specific gene 6) (Non-patent Document 4). Receptor tyrosine kinases, such as Sky, Mer, and AXL, are known as receptor tyrosine kinases with Gas6 as a ligand (Non-patent Document 5).

AXL is presumed to have molecular functions involved in cell growth enhancement, suppression of apoptosis, cell migration, and cell adhesion. Experimentally observed phenomena in cells treated with Gas6 protein support this presumption. Reported experimental results include its suppression of cell death and its enhancement of cell growth in rat vascular smooth muscle (Non-patent Documents 6 and 7), the acceleration of cell growth and the suppression of cell death after serum starvation in mouse NIH3T3 cells (Non-patent Documents 8 and 9), the promotion of cell growth in mouse cardiac fibroblasts (Non-patent Document 10), the enhancement of cell growth in human prostate cancer cells (Non-patent Document 11), the enhancement of cell growth and infiltration and the suppression of cell death in human gastric carcinoma cells (Non-patent Document 12), the enhancement of the migration ability of human and rat vascular smooth muscle cells (Non-patent Document 13), the enhancement of the cell migration ability of mouse neurons (Non-patent Document 14), and the aggregation of cells highly expressing mouse AXL (Non-patent Document 15).

Similarly, PI3K-Akt pathway and MAPK pathway are said to function as downstream pathways of the signal transduction mediated by AXL based on molecular analyses of intracellular signals after treatment with Gas6 (Non-patent Document 5). An analysis with a yeast two-hybrid method using an AXL intracellular region as the bait confirmed the direct molecular interactions with these downstream pathways. As a result, GrbB2/PI3K/p55γ/SOCS-1/NcK2/RanBP2/C1-TEN were identified (Non-patent Document 16). The interactions of these molecules suggest the presence of intracellular signal transduction pathways as downstream from the AXL signal. Furthermore, the observed interactions support the presumption that AXL functions in cell growth enhancement, the suppression of apoptosis, cell migration, and cell adhesion. AXL has also been identified as a gene highly expressed when TNFα-induced cell death of mouse fibroblasts is suppressed by IL-15. The suppression of TNFα-induced cell death was abolished by suppressing AXL expression, and the phosphorylation of IL-15 receptors and AXL was enhanced by treatment with IL-15. These experimental findings also suggest that signal transduction is mediated by the complex of AXL and IL-15 receptor (Non-patent Document 17).

Tumorigenicity of nude mice has been reported to dissipate as a result of inhibiting Gas6-dependent phosphorylation of AXL in human glioma lines overexpressing the AXL dominant negative form (Non-patent Document 18). However, there have been no reports or suggestions and remain unclear whether any anti-AXL antibody which inhibits phosphorylation exists.

AXL is a single-pass transmembrane receptor tyrosine kinase, and the extracellular region is composed of two immunoglobulin-like domains (referred to as IgD1 and IgD2) and two fibronectin type III domains (referred to as FND1 and FND2) from the N-terminal side (Non-patent Document 3). Although FND is known to be expressed in molecules such as neural cell adhesion molecules and nephrins involved in intercellular adhesion, detailed functions of FND in AXL are unclear (Non-patent Document 19).

AXL has been identified as an oncogene that retains an inherent ability to transform cells, and has been studied as a carcinogenesis-related molecule. Many analyses of AXL expression have been reported on the protein and mRNA. The high expression of AXL protein has been reported in human tumor tissues and tumor cells, including lung cancer (Non-patent Document 20), breast cancer (Non-patent Document 21), ovarian cancer (Non-patent Document 22), thyroid cancer (Non-patent Document 23), melanoma (Non-patent Document 23), renal cancer (Non-patent Document 24), gastric cancer (Non-patent Document 12), and glioma (Non-patent Document 25). Furthermore, the high expression of AXL protein is suggested by high levels of AXL mRNA in esophageal cancer (Non-patent Document 26), colon cancer (Non-patent Document 27), and acute myeloid leukemia (Non-patent Document 28). There are also reports of the inhibition of lumen formation via the suppression of AXL by RNAi in HUVEC (Non-patent Document 29), the reduced tumor-forming ability of human breast cancer cells in mice resulting from the constitutive suppression of AXL (Non-patent Document 29), and the reduced tumor-forming ability of human glioma cells in mice resulting from the constitutive high expression of dominant negative mutants (Non-patent Document 25). The involvement of AXL molecular functions in tumor growth is strongly suggested.

Polyclonal antibodies to the extracellular domain of AXL have been reported to have a migration inhibitory action on highly invasive breast cancer cell lines (Patent Document 1). However, non-clinical studies showed that drugs demonstrating cancer-cell-migration-inhibitory action do not necessarily demonstrate antitumor activity. For example, matrix metalloproteinase (hereinafter abbreviated to "MMP") has been known to promote tumor infiltration and migration. Thus, attention has been focused on various matrix metalloproteinase inhibitors that inhibit the enzyme activity of MMP, and clinical studies have been conducted on various pharmaceutical agents such as Batimastat, Marimastat, and Prinomastat. However, antitumor effects have not been observed in the clinical trials (Non-patent Document 30).

Accordingly, there have been no reports or suggestions and it remains unknown whether anti-AXL antibodies have antitumor effects particularly in vivo, whether they can suppress angiogenesis, and whether they can suppress cancer.

Patent Document 1: WO 2004/008147
Non-patent Document 1: Liu, et al., Proc. Natl Acad. Sci. U.S.A. (1988) 85, 1952-6
Non-patent Document 2: Janssen, et al., Oncogene (1991) 6, 2113-20
Non-patent Document 3: O'Bryan, et al., Mol. Cell. Biol. (1991) 11, 5016-31
Non-patent Document 4: Varnum, et al., Nature (1995) 373, 623-626
Non-patent Document 5: Hafizi, et al., FEBS J. (2006) 273, 5231-5244
Non-patent Document 6: Nakano, et al., FEBS Lett. (1996) 387, 78-80
Non-patent Document 7: Nakano, et al., J. Biol. Chem. (1995) 270, 5702-5
Non-patent Document 8: Goruppi, et al., Mol. Cell. Biol. (1997) 17, 4442-53
Non-patent Document 9: Bellosta, et al., Oncogene (1997) 15, 2387-97
Non-patent Document 10: Stenhoff, et al., Biochem. Biophys. Res. Commun. (2004) 319, 871-8
Non-patent Document 11: Sainaghi, et al., J. Cell. Physiol. (2005) 204, 36-44
Non-patent Document 12: Sawabu, et al., Mol. Carcinog. (2007) 46, 155-164
Non-patent Document 13: Fridell, et al., J. Biol. Chem. (1998) 273, 7123-6
Non-patent Document 14: Allen, et al., Mol. Cell. Biol. (2002) 22, 599-613
Non-patent Document 15: McCloskey, et al., J. Biol. Chem. (1997) 272, 23285-91
Non-patent Document 16: Hafizi, et al., Biochem. Biophys. Res. Commun. (2002) 299, 793-800
Non-patent Document 17: Budagian et al., Embo J. (2005) 24, 4260-70
Non-patent Document 18: Vajkoczy P et al., Proc. Natl Acad. Sci. U.S.A. (2006) 103, 5799-804
Non-patent Document 19: Yamagata et al., Curr. Opin. Cell. Biol. (2003) 15, 621-632
Non-patent Document 20: Shieh, et al., Neoplasia (2005) 7, 1058-1064
Non-patent Document 21: Meric, et al., Clin. Cancer Res. (2002) 8, 361-367
Non-patent Document 22: Sun, et al., Oncology (2004) 66, 450-457
Non-patent Document 23: Ito, et al., Thyroid (2002) 12, 971-975
Non-patent Document 24: Chung, et al., DNA Cell Biol. (2003) 22, 533-540
Non-patent Document 25: Vajkoczy, et al., Proc. Natl. Acad. Sci. U.S.A. (2006) 103, 5799-804
Non-patent Document 26: Nemoto, et al., Pathobiology (1997) 65, 195-203
Non-patent Document 27: Craven, et al., Int. J. Cancer (1995) 60, 791-797
Non-patent Document 28: Neubauer, et al., Blood (1994) 84, 1931-1941
Non-patent Document 29: Holland, et al., Cancer Res. (2005) 65, 9294-9303
Non-patent Document 30: Pavlaki et al., Cancer Metastasis Rev. (2003) 22, 177-203

DISCLOSURE OF THE INVENTION

Problems to be Solved by the Invention

The objectives of the present invention are to provide anti-AXL antibodies and uses thereof. More specifically, the objectives of the present invention are to provide methods for inhibiting angiogenesis using anti-AXL antibodies, methods for suppressing cell growth, methods for inhibiting AXL function, methods for accelerating AXL function, and methods for reducing the AXL expression level. A further objective of the present invention is to provide anti-AXL antibodies with novel effects.

Means for Solving the Problems

As a result of conducting dedicated studies, the present inventors succeeded in producing anti-AXL antibodies with specific functions and discovered that these antibodies have an angiogenesis-suppressive effect and an antitumor effect, and they therefore completed the present invention. More specifically, the present invention includes:

[1] a monoclonal antibody that binds to AXL;
[2] the antibody according to [1], which has cell-growth-suppressive activity;
[3] the antibody according to [1], which suppresses cancer cell growth;
[4] the antibody according to any of [1] to [3], which binds to FND1;
[5] an antibody prepared using as an antigen a peptide comprising entire FND1 or a sequence comprising at least five or more consecutive amino acids thereof;
[6] the antibody according to any of [1] to [5], which has agonistic activity for AXL;
[7] the antibody according to any of [1] to [5], which has antagonistic activity for AXL;
[8] the antibody according to [7], which is obtained by selecting an antibody in which phosphorylated tyrosine is not detected in AXL when contacting it to an AXL-expressing cell together with an AXL ligand;
[9] the antibody according to any of [1] to [8], which has an activity that reduces AXL expression level;
[10] the antibody according to any of [1] to [9], which has angiogenesis inhibitory activity;
[11] an antibody according to any of the following (a) to (j):
(a) an antibody (Ax285) produced from a hybridoma deposited under Accession No. FERM BP-10858;
(b) an antibody (Ax292) produced from a hybridoma deposited under Accession No. FERM BP-10859;
(c) an antibody (Ax223) produced from a hybridoma deposited under Accession No. FERM BP-10853;
(d) an antibody (Ax96) produced from a hybridoma deposited under Accession No. FERM BP-10852;
(e) an antibody (Ax258) produced from a hybridoma deposited under Accession No. FERM BP-10856;
(f) an antibody (Ax284) produced from a hybridoma deposited under Accession No. FERM BP-10857;
(g) an antibody (Ax7) produced from a hybridoma deposited under Accession No. FERM BP-10850;
(h) an antibody (Ax51) produced from a hybridoma deposited under Accession No. FERM BP-10851;
(i) an antibody (Ax225) produced from a hybridoma deposited under Accession No. FERM BP-10854; and
(j) an antibody (Ax232) produced from a hybridoma deposited under Accession No. FERM BP-10855;
[12] an antibody that binds to the same epitope as an epitope bound by any of the antibodies according to [11];
[13] an antibody that comprises a CDR sequence identical to a CDR sequence comprised in any of the antibodies according to [11];
[14] an antibody in which sequences of heavy chain CDR1, 2, and 3 are SEQ ID NOs: 4, 5, and 6, respectively;

[15] an antibody that comprises a heavy chain CDR comprising an amino acid sequence of the heavy chain CDR of the antibody according to [14] with a substitution, deletion, insertion, and/or addition of one or more amino acids, and is functionally equivalent with the antibody according to [14];
[16] an antibody in which sequences of light chain CDR1, 2, and 3 are SEQ ID NOs: 8, 9, and 10, respectively;
[17] an antibody that comprises a light chain CDR comprising an amino acid sequence of the light chain CDR of the antibody according to [16] with a substitution, deletion, insertion, and/or addition of one or more amino acids, and is functionally equivalent with the antibody according to [16];
[18] the antibody according to any of [13] to [17] that is a chimeric antibody;
[19] the antibody according to any of [13] to [17] that is a humanized antibody;
[20] a hybridoma according to any of the following (a) to (j):
(a) a hybridoma deposited under Accession No. FERM BP-10858 (Ax285);
(b) a hybridoma deposited under Accession No. FERM BP-10859 (Ax292);
(c) a hybridoma deposited under Accession No. FERM BP-10853 (Ax223);
(d) a hybridoma deposited under Accession No. FERM BP-10852 (Ax96);
(e) a hybridoma deposited under Accession No. FERM BP-10856 (Ax258);
(f) a hybridoma deposited under Accession No. FERM BP-10857 (Ax284);
(g) a hybridoma deposited under Accession No. FERM BP-10850 (Ax7);
(h) a hybridoma deposited under Accession No. FERM BP-10851 (Ax51);
(i) a hybridoma deposited under Accession No. FERM BP-10854 (Ax225); and
(j) a hybridoma deposited under Accession No. FERM BP-10855 (Ax232);
[21] an angiogenesis inhibitor that comprises an anti-AXL antibody as an active ingredient;
[22] the angiogenesis inhibitor according to [21], wherein the antibody is an antibody according to any of [1] to [19];
[23] a cell-growth suppressant that comprises an anti-AXL antibody as an active ingredient;
[24] the suppressant according to [23], wherein the cells are cancer cells;
[25] the suppressant according to [23], wherein the antibody is an antibody according to any of [1] to [19];
[26] the suppressant according to [23], wherein the anti-AXL antibody is an antibody that binds to FND1;
[27] the suppressant according to [23], which comprises as an active ingredient an antibody that binds to IgD2 and has a phosphorylation-inhibition activity;
[28] an AXL phosphorylation activity inducer, which comprises an anti-AXL antibody as an active ingredient;
[29] the inducer according to [28], wherein the anti-AXL antibody is an antibody that binds to IgD;
[30] the inducer according to [28], wherein the antibody is an antibody according to [6];
[31] an AXL phosphorylation activity inhibitor, which comprises an anti-AXL antibody as an active ingredient;
[32] the inhibitor according to [31], wherein the anti-AXL antibody is an antibody that binds to IgD2;
[33] the inhibitor according to [31], wherein the antibody is an antibody according to [7] or [8];
[34] an agent that reduces an AXL expression level, which comprises an anti-AXL antibody as an active ingredient;
[35] the agent for reducing an expression level according to [34], wherein the anti-AXL antibody is an antibody that binds to FND1;
[36] the agent that reduces the expression level according to [34], wherein the antibody is an antibody according to [9];
[37] a method for inducing phosphorylation of AXL using an anti-AXL antibody;
[38] a method for reducing an AXL expression level using an anti-AXL antibody;
[39] a method for inhibiting the phosphorylation of AXL using an anti-AXL antibody;
[40] an anti-cancer agent that comprises an anti-AXL antibody as an active ingredient;
[41] the anti-cancer agent according to [40], wherein the antibody is an antibody according to any of [1] to [19];
[42] The anti-cancer agent according to [40], which comprises as an active ingredient an antibody that binds to IgD2 and has a phosphorylation-inhibition activity;
[43] the anti-cancer agent according to [40], wherein the cancer is pancreatic cancer, gastric cancer, lung cancer, osteosarcoma, colon cancer, prostate cancer, melanoma, endometrial cancer, ovarian cancer, uterine leiomyoma, thyroid cancer, cancer stem cell, breast cancer, bladder cancer, renal cancer, glioma, neuroblastoma, or esophageal cancer;
[44] the anti-cancer agent according to [42], wherein the cancer is glioma, gastric cancer, endometrial cancer, non-small-cell lung cancer, pancreatic adenocarcinoma, or breast cancer;
[45] the anti-cancer agent according to [43], wherein the cancer is pancreatic adenocarcinoma or breast cancer;
[46] the antibody according to [1], which has an AXL phosphorylation-inhibition activity;
[47] a method for inhibiting angiogenesis using an anti-AXL antibody;
[48] a method for using an anti-AXL antibody in manufacturing an angiogenesis inhibitor;
[49] a method for suppressing cell growth using an anti-AXL antibody;
[50] a method for treating and/or preventing cancer using an anti-AXL antibody;
[51] a method for using an anti-AXL antibody in manufacturing a cell-growth suppressant;
[52] a method for using an anti-AXL antibody in manufacturing an anti-cancer agent;
[53] a method for using an anti-AXL antibody in manufacturing a phosphorylation inducer;
[54] a method for using an anti-AXL antibody in manufacturing a phosphorylation inhibitor;
[55] a method for using an anti-AXL antibody in manufacturing an agent for lowering the AXL expression level; and
[56] a method for producing an anti-AXL specific antibody comprising:
(a) immunizing a non-human animal with a peptide comprising entire FND1 or a sequence comprising at least five or more consecutive amino acids thereof; and
(b) collecting an antibody from the non-human animal of (a) or collecting an antibody-producing cell to collect an antibody produced by the antibody-producing cell.

BRIEF DESCRIPTION OF THE DRAWINGS

FIG. 6 is a table showing the antitumor effects of anti-AXL monoclonal antibodies of the present invention (Ax223, Ax285, Ax96, Ax292, Ax258, Ax7, Ax51, Ax284, and Ax225) (2) in a mouse xenograft model of human pancreatic adenocarcinoma, and summarizing the binding domain and phosphorylation-inhibiting activity of each antibody.

DETAILED DESCRIPTION

Figure 1A:
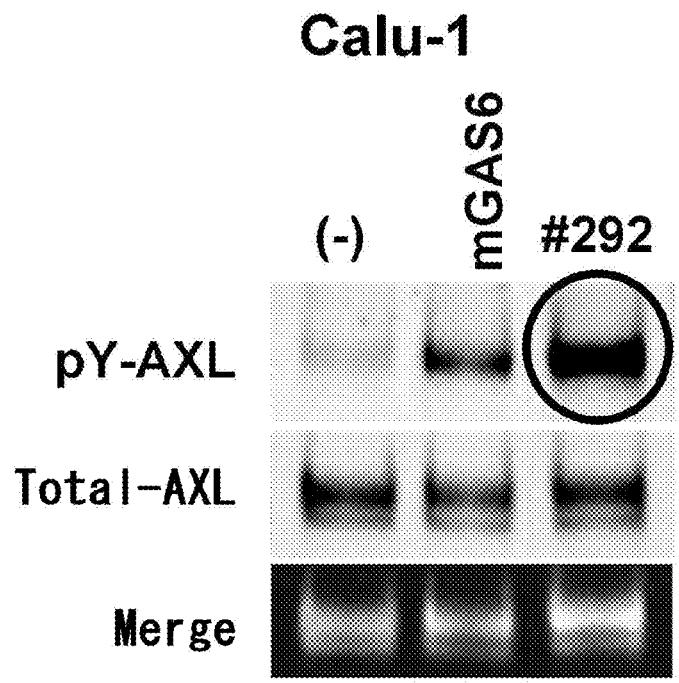
FIG. 1A is a photograph showing the activity of an anti-AXL monoclonal antibody (Ax292) of the present invention, in inducing AXL phosphorylation in cancer cells. The antibody was shown to induce the phosphorylation of a kinase domain of AXL.
Figure 1B:
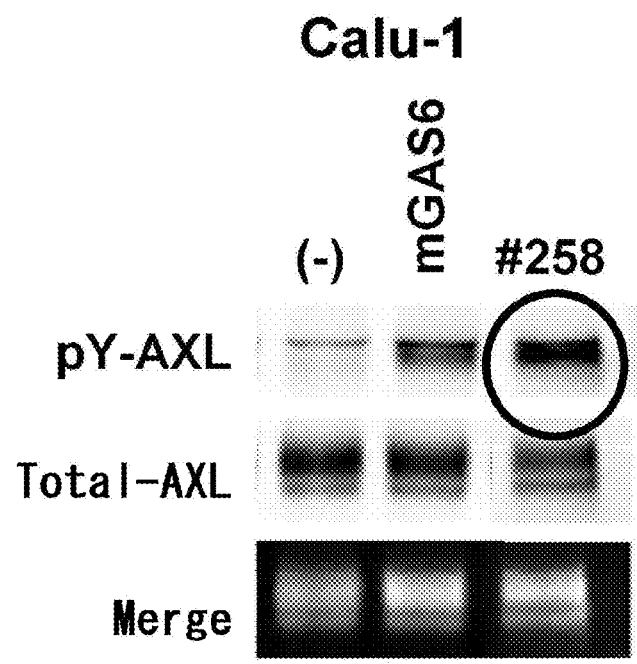
FIG. 1B is a photograph showing the activity of an anti-AXL monoclonal antibody (Ax258) of the present invention, in inducing AXL phosphorylation in cancer cells. The antibody was shown to induce the phosphorylation of a kinase domain of AXL.
Figure 1C:
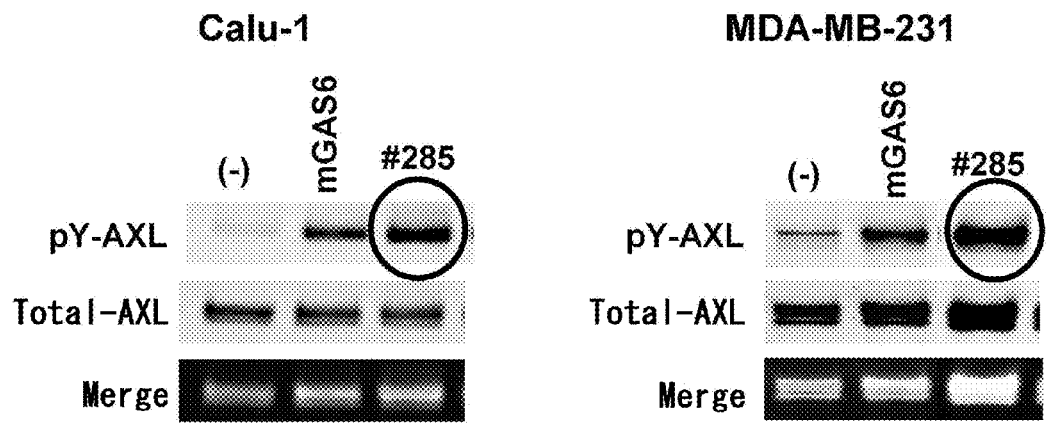
FIG. 1C is a photograph showing the activity of an anti-AXL monoclonal antibody (Ax285) of the present invention, in inducing AXL phosphorylation in cancer cells. The antibody was shown to induce the phosphorylation of a kinase domain of AXL.
Figure 1D:
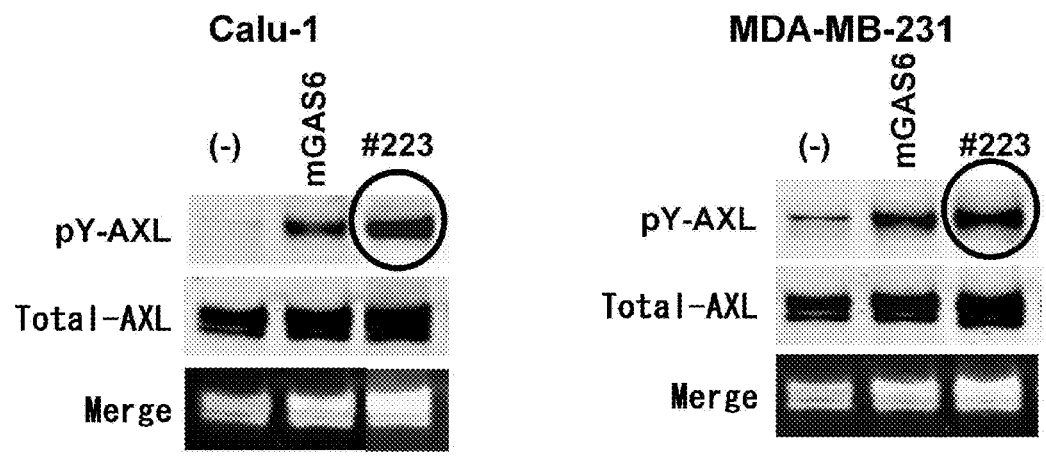
FIG. 1D is a photograph showing the activity of an anti-AXL monoclonal antibody (Ax223) of the present invention, in inducing AXL phosphorylation in cancer cells. The antibody was shown to induce the phosphorylation of a kinase domain of AXL.
Figure 1E:
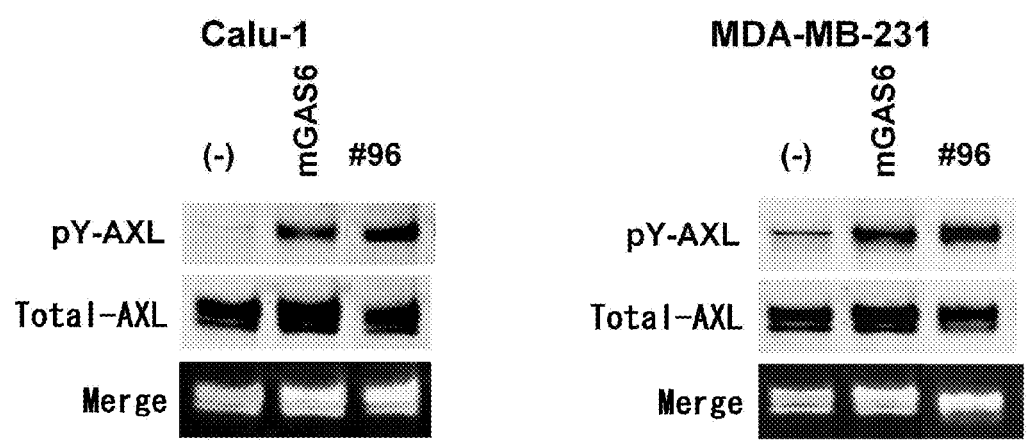
FIG. 1E is a photograph showing the activity of an anti-AXL monoclonal antibody (Ax96) of the present invention, in inducing AXL phosphorylation in cancer cells. The antibody was shown to induce the phosphorylation of a kinase domain of AXL.

A novel anti-AXL antibody is provided by the present invention. Moreover, a novel use of the anti-AXL antibody is provided by the present invention.

There are no particular limitations on the anti-AXL antibody of the present invention so long as it binds to AXL, and there are also no particular limitations on its origin (such as human, mouse, rat, rabbit, or chicken), type (polyclonal antibody or monoclonal antibody), form (such as an altered antibody, modified antibody, antibody fragment, or minibody [low-molecular-weight antibody]), or such. Although there are no particular limitations on the anti-AXL antibody of the present invention, the antibody preferably specifically binds to anexelekto and is preferably a monoclonal antibody.

The anti-AXL antibody of the present invention also preferably has a cell-growth-suppressive activity.

A preferable embodiment of the anti-AXL antibodies of the present invention is anti-AXL antibodies binding to FND1.

As is clear from the Examples described later, antibodies that bind to FND1 in particular have significantly high in vivo antitumor activity compared to those of other antibodies.

Binding activity of anti-AXL antibodies to FND1 can be evaluated by a method known to those skilled in the art, for example, the methods described below. Binding activity of anti-AXL antibody to FND1 is confirmed by electrophoresing FND1 and western blotting with anti-AXL antibody.

An anti-AXL antibody with agonistic activity for AXL is an example of the preferable embodiment of the anti-AXL antibody of the present invention. An anti-AXL antibody with agonistic activity for AXL refers to the induction of phosphorylation mediated by AXL, and particularly to the induction of the phosphorylation reaction of tyrosine, when the anti-AXL antibody binds to AXL. Although there are no particular limitations on the target of the phosphorylation reaction that is induced by the anti-AXL antibody with agonistic activity, an example includes the autophosphorylation of AXL.

Whether or not an anti-AXL antibody has agonistic activity can be determined with a method known by those skilled in the art, for example, by the method described below. A test anti-AXL antibody is contacted with cells expressing AXL (such as Calu-1, MDA-MB-231, or DU-145 cells), and AXL is subsequently extracted from the cells. The tyrosine in the extracted AXL is confirmed to be phosphorylated using an anti-phosphotyrosine antibody. More specifically, an anti-AXL antibody can be confirmed as having an agonistic activity with the methods described in the Examples.

Examples of anti-AXL antibodies with agonistic activity include the antibodies (a) to (g) below:
(a) an antibody produced from a hybridoma deposited under Accession No. FERM BP-10858 (Ax285);
(b) an antibody produced from a hybridoma deposited under Accession No. FERM BP-10852 (Ax96);
(c) an antibody produced from a hybridoma deposited under Accession No. FERM BP-10856 (Ax258);
(d) an antibody produced from a hybridoma deposited under Accession No. FERM BP-10859 (Ax292);
(e) an antibody produced from a hybridoma deposited under Accession No. FERM BP-10853 (Ax223);
(f) an antibody recognizing the same epitope as the epitope recognized by an antibody of any one of (a) to (e); and
(g) an antibody with a CDR sequence identical to the CDR sequence of an antibody of any one of (a) to (e).

An antibody recognizing the same epitope as an antibody described above can be obtained according to, for example, the method described below.

Whether a test antibody shares an epitope with a certain antibody can be confirmed by the competition of the two antibodies for the same epitope. Competition between antibodies is detected with a cross-blocking assay or the like. A competitive ELISA, for example, is a preferable cross-blocking assay. Specifically, in a cross-blocking assay, AXL protein coated onto the wells of a microtiter plate is preincubated in the presence or absence of the candidate competitive antibody, then an anti-AXL antibody, as indicated above, is added. The amount of the aforementioned anti-AXL antibody bound to the AXL protein in the wells is indirectly correlated to the binding ability of the candidate competitive antibody (test antibody) competing for binding to the same epitope. Thus, the greater the affinity of the test antibody for the same epitope, the greater is the reduction in the amount of the aforementioned anti-AXL antibody bound to the wells coated with AXL protein and the greater the increase in the amount of test antibody bound to the wells coated with AXL protein.

The amount of antibody bound to the wells can be measured easily by labeling the antibody in advance. For example, a biotin-labeled antibody can be measured using an avidin-peroxidase conjugate and a suitable substrate. A cross-blocking assay that uses an enzyme label such as peroxidase is specifically referred to as a competitive ELISA. The antibody can be labeled with other labeling substances that can be detected or measured. Specifically, radioactive labels and fluorescent labels are known.

When the test antibody has a constant region derived from a species differing from that of the anti-AXL antibody indicated above, the amount of antibody bound to the wells can also be measured with a labeled antibody that recognizes the constant region of that antibody. Alternatively, when an antibody is derived from the same species but is of a different class, the amount of antibody bound to the wells can be measured with antibodies that recognize each class.

If a candidate competitive antibody can block the binding of the anti-AXL antibody by at least 20%, preferably by at least 20%-50%, and more preferably by at least 50% compared with the binding activity achieved in a control test performed in the absence of the candidate competitive antibody, then the candidate competitive antibody is an antibody that substantially binds to the same epitope or that competes for binding to the same epitope as the aforementioned anti-AXL antibody.

The determination of a CDR sequence to obtain an antibody with a CDR sequence identical to that of a certain antibody can be performed by one skilled in the art according to known methods. For example, a CDR sequence can be determined by determining the full-length amino acid sequence of an antibody or the amino acid sequence of a variable region, and investigating its homology by applying the determined amino acid sequence to the database of antibody amino acid sequences developed by Kabat et al. ("Sequence of Proteins of Immunological Interest", US Dept. of Health and Human Services, 1983). The numbers in the framework and the numbers in the CDR sequence can be determined according to the definition of Kabat (Kabat, A. E. et al., US Dept. of Health and Human Services, US Government Printing Offices, 1991).

The full-length amino acid sequence of an antibody or the amino acid sequence of a variable region can be determined by one skilled in the art in accordance with known methods.

An antibody with a CDR sequence identical to that of a certain antibody may have an identical sequence in at least one CDR of the six CDRs that are present in the antibody. However, the antibody preferably has an identical sequence in all three CDRs present in the heavy chain or an identical sequence in all three CDRs present in the light chain, and even more preferably, the antibody has an identical sequence in all six CDRs present in the antibody.

Antibodies with a CDR sequence that is identical to a CDR sequence of a certain antibody include chimeric antibodies and humanized antibodies. Chimeric antibodies and humanized antibodies will be described below.

An example of another preferable embodiment of the anti-AXL antibody of the present invention is an anti-AXL antibody with antagonistic activity against AXL. An anti-AXL antibody with antagonistic activity against AXL refers to an antibody with activity that inhibits the phosphorylation reaction mediated by AXL induced by the binding of an AXL ligand (such as Gas6) to AXL, and particularly the tyrosine phosphorylation reaction. The inhibition of the phosphorylation reaction can be carried out by inhibiting the binding between the AXL ligand and AXL, or by another method. Although there are no particular limitations on the subjects of phosphorylation inhibition reaction induced by an anti-AXL antibody with antagonistic activity, examples include the autophosphorylation of AXL.

Whether an anti-AXL antibody has antagonistic activity can be determined by a method known to those skilled in the art, and for example, by the method described below. A test antibody is contacted with cells expressing AXL (such as Calu-1, MDA-MB-231, or DU-145 cells) together with an AXL ligand, and AXL is subsequently extracted from the cells. Phosphorylated tyrosine is confirmed not to be detected in the extracted AXL using an anti-phosphotyrosine antibody. More specifically, an anti-AXL antibody can be confirmed as having antagonistic activity using the methods described in the Examples.

Examples of anti-AXL antibodies with antagonistic activity include antibodies (a) to (d) below:
(a) an antibody produced from a hybridoma deposited under Accession No. FERM BP-10850 (Ax7);
(b) an antibody produced from a hybridoma deposited under Accession No. FERM BP-10851 (Ax51);
(c) an antibody recognizing the same epitope as the epitope recognized by an antibody of any one of (a) to (b); and
(d) an antibody having a CDR sequence identical to the CDR sequence of an antibody of any one of (a) to (c).

An antibody recognizing the same epitope and an antibody with an identical CDR sequence can be obtained with the methods previously described.

An antibody with antagonistic activity is useful for inhibiting angiogenesis, suppressing cell growth, and the like.

An example of another preferable embodiment of the antibody of the present invention is an antibody with activity that reduces the AXL expression level. In the present invention, reducing the expression level of AXL can indicate a reduction in the amount of AXL already present through the degradation of AXL or such, or can indicate a reduction in the amount of newly expressed AXL by suppressing the expression of AXL. Whether the AXL expression level has decreased can be confirmed by a method known to those skilled in the art, and for example, by the method described below. A test anti-AXL antibody is contacted with cells expressing AXL (such as Calu-1, MDA-MB-231, or DU-145 cells), and the amount of AXL present in the cells is subsequently detected by immunoblotting or such. A comparison is then made between the amount of AXL detected when the test antibody is contacted and the amount of AXL detected when the test antibody is not contacted. More specifically, this can be confirmed according to methods described in the Examples.

Examples of anti-AXL antibodies with activity that reduces AXL expression levels include antibodies (a) to (j) below:
(a) an antibody (Ax285) produced from a hybridoma deposited under Accession No. FERM BP-10858;
(b) an antibody (Ax96) produced from a hybridoma deposited under Accession No. FERM BP-10852;
(c) an antibody (Ax258) produced from a hybridoma deposited under Accession No. FERM BP-10856;
(d) an antibody (Ax7) produced from a hybridoma deposited under Accession No. FERM BP-10850;
(e) an antibody (Ax292) produced from a hybridoma deposited under Accession No. FERM BP-10859;
(f) an antibody (Ax223) produced from a hybridoma deposited under Accession No. FERM BP-10853;
(g) an antibody (Ax225) produced from a hybridoma deposited under Accession No. FERM BP-10854;
(h) an antibody (Ax284) produced from a hybridoma deposited under Accession No. FERM BP-10857;
(i) an antibody recognizing the same epitope as the epitope recognized by an antibody of any one of (a) to (h); and
(j) an antibody having a CDR sequence identical to the CDR sequence of an antibody of any one of (a) to (i).

An antibody recognizing the same epitope and an antibody having an identical CDR sequence can be obtained with the methods previously described.

An antibody with an activity that reduces the AXL expression level is useful for inhibiting angiogenesis, suppressing cell growth, and the like.

An example of another preferable embodiment of the antibody of the present invention is an antibody with an angiogenesis-inhibiting effect. Although there are no particular limitations on the angiogenesis-inhibiting effect of the present invention, so long as the new formation of blood vessels is inhibited, examples include an inhibitory effect on the migration activity of vascular endothelial cells, an apoptosis-inducing effect on vascular endothelial cells, and an inhibitory effect on the vascular morphogenesis of vascular endothelial cells. A preferred example of an antibody with an angiogenesis-inhibiting effect is an antibody with an angiogenesis-inhibiting effect on tumor tissues. There are no particular limitations on the tumor tissues, and examples include pancreatic cancer tissue (such as pancreatic adenocarcinoma tissue), gastric cancer tissue, lung cancer tissue (tissues of small-cell lung cancer, non-small-cell lung cancer, and such), osteosarcoma tissue, colon cancer tissue, prostate cancer tissue, melanoma tissue, endometrial cancer tissue, ovarian cancer tissue, uterine leiomyoma tissue, thyroid cancer tissue, cancer stem cell tissue, breast cancer tissue, bladder cancer tissue, renal cancer tissue, glioma tissue, neuroblastoma tissue, and esophageal cancer tissue. More preferable tissues are glioma tissue, gastric cancer tissue, endometrial cancer tissue, non-small-cell lung cancer tissue, pancreatic adenocarcinoma tissue, and breast cancer tissue, particularly pancreatic adenocarcinoma tissue and breast cancer tissue.

Whether or not an antibody has an angiogenesis-inhibiting effect can be confirmed by a method known to those skilled in the art, and for example, this can be confirmed using a commercially available angiogenesis kit. More specifically, this can be confirmed with the methods described in the Examples.

Specific examples of antibodies with angiogenesis-inhibiting effects include the previously described antibodies.

An example of another preferable embodiment of the antibody of the present invention is an antibody with cell-growth-suppressive activity.

Although there are no particular limitations on the cells whose growth is suppressed by the anti-AXL antibody, they are preferably cells related to a disease, and more preferably cancer cells. When the cells are cancer cells, there are no particular limitations on the type of cancer, and examples include pancreatic cancer (such as pancreatic adenocarcinoma), gastric cancer, lung cancer (small-cell lung cancer, non-small-cell lung cancer, and such), osteosarcoma, colon cancer, prostate cancer, melanoma, endometrial cancer, ovarian cancer, uterine leiomyoma, thyroid cancer, cancer stem cell, breast cancer, bladder cancer, renal cancer, glioma, neuroblastoma, and esophageal cancer. More preferable cancers are glioma, gastric cancer, endometrial cancer, non-small-cell lung cancer, pancreatic adenocarcinoma, and breast cancer, particularly pancreatic adenocarcinoma and breast cancer.

There are no particular limitations on the mechanism for the suppression of cell growth by the antibody of the present invention, and cell growth can be suppressed by any mechanism, such as the inhibition of angiogenesis, the inhibition of phosphorylation, the induction of phosphorylation, or the reduction of the AXL expression level.

The following methods are preferably used to evaluate or measure the cell-growth-suppressive effects based on the anti-AXL antibody.

As a method of evaluating or measuring cell-growth-suppressive activity in vitro, a method is used in which the uptake by viable cells of [$^3$H]-labeled thymidine added to their medium is measured as an indicator of DNA replication ability. As a simpler method, a dye expulsion method is used, in which the ability to exclude a dye such as Trypan Blue outside from the cells is measured under a microscope, or an MTT method is used. The latter uses the ability of living cells to convert MTT (3-(4,5-dimethylthiazol-2-yl)-2,5-diphenyl tetrazolium bromide), a tetrazolium salt, to a blue formazan product. Specifically, a test antibody is added to the culture solution of the test cells together with a ligand, and after a predetermined period of time, MTT solution is added to the culture solution and this is left to stand for a predetermined period to allow the MTT to be incorporated into the cells. The MTT, which is a yellow compound, is converted to a blue compound by succinate dehydrogenase in the mitochondria of the cells. After the dissolution of this blue product and coloration, the absorbance is measured and used as an indicator of the number of viable cells. Besides MTT, reagents such as MTS, XTT, WST-1, and WST-8 are commercially available (Nacalai Tesque, and such) and can be appropriately used. A control antibody can also be used when measuring this activity.

A tumor-bearing mouse model can be used to evaluate or measure the cell-growth-suppressive activity in vivo. For example, after cancer cells expressing AXL are transplanted into a non-human test animal, either intradermally or subcutaneously, a test antibody is administered intravenously or intraperitoneally starting from the day of transplantation or from the following day, either daily or at intervals of a few days. The cell-growth-suppressive activity can be evaluated by measuring the tumor size over time. In a similar manner to the evaluation in vitro, cell-growth-suppressive activity can be determined by administering a control antibody and observing whether the tumor size in the anti-AXL antibody-administered group is significantly smaller than the tumor size in the control antibody-administered group. When a mouse is used as the non-human test animal, nude (nu/nu) mice can be suitably used, in which T-lymphocyte function has been lost due to a genetic deficiency in the thymus. The use of these mice makes it possible to eliminate the involvement of T lymphocytes in the test animal during the evaluation and measurement of the cell-growth-suppressive activity of the administered antibody.

Examples of anti-AXL antibodies with cell-growth-suppressive effects include the previously described antibodies.

The anti-AXL monoclonal antibody of the present invention can be acquired using known methods. A monoclonal antibody derived from a mammal is particularly preferable as the anti-AXL antibody of the present invention. Monoclonal antibodies derived from mammals include those produced from hybridomas as well as those produced by a host transformed with an expression vector containing the antibody genes, using genetic engineering techniques.

A monoclonal-antibody-producing hybridoma can be generated using known technology, such as that described below. First, AXL protein is used as the sensitizing antigen for immunization according to ordinary immunization methods. Immune cells obtained from an immunized animal are then fused with known parent cells, according to ordinary cell fusion methods, to obtain hybridomas. A hybridoma that produces the anti-AXL antibody can be selected from these hybridomas by screening for cells that produce the target antibody using ordinary screening methods.

More specifically, monoclonal antibodies can be generated out according to, for example, the method described below. First, the AXL protein that is used as the sensitizing antigen for obtaining the antibodies can be obtained by expressing the AXL gene. The nucleotide sequence of the human AXL gene is already known (GenBank Accession No. M76125). After inserting the gene sequence encoding AXL into a known expression vector with which to transform suitable host cells, the human AXL protein of interest can be purified from the host cells or from the culture supernatant using known methods. Purified naturally occurring AXL protein can also be used in the same manner. Purification can be carried out by using several chromatographies, such as the usual ion chromatography and affinity chromatography, performed once or multiple times, either in combination or alone. A fusion protein, in which the desired partial polypeptide of the AXL protein is fused to a different polypeptide, can also be used as an immunogen. An antibody Fc fragment or peptide tag, or the like, can be used to produce a fusion protein for use as an immunogen. A vector that expresses a fusion protein can be produced by fusing two or more types of desired genes encoding polypeptide fragments in frame and inserting the fused genes into an expression vector, as previously described. Methods of preparing fusion proteins are described in Molecular Cloning, 2nd edition (Sambrook, J. et al., Molecular Cloning 2nd ed., 9.47-9.58, Cold Spring Harbor Laboratory Press, 1989). AXL protein purified in this manner can be used as a sensitizing antigen for the immunization of a mammal.

A partial peptide of AXL can also be used as a sensitizing antigen. Examples of partial peptides of AXL include a peptide obtained by chemical synthesis from an amino acid sequence of human AXL, a peptide obtained by incorporating a portion of the human AXL gene into an expression vector and expressing it, and a peptide obtained by degrading human AXL protein using a protease. There are no particular limitations on the region used as the partial peptide, and an extracellular region of AXL, for example, can be used.

Moreover, a peptide having the sequence of entire FND1 or containing at least its five consecutive amino acids can be preferably used as a partial peptide. Sequences containing at least five consecutive amino acids refer to those preferably containing six or more and more preferably eight or more consecutive amino acids. In addition, sequences containing at least five or more consecutive amino acids refer to amino acid sequences having antigenicity.

There are no particular limitations on the mammal immunized with the sensitizing antigen. To obtain a monoclonal antibody by cell fusion, it is preferable to select an animal to be immunized after consideration of its compatibility with the parent cells used for the cell fusion. In general, rodents are preferred as the immunized animal. More specifically, mice, rats, hamsters, or rabbits can be used for as the immunized animal. Monkeys and the like can also be used as the immunized animal.

The animal described above can be immunized with a sensitizing antigen using known methods. For example, in a typical method, the mammal is immunized by injecting the sensitizing antigen intraperitoneally or subcutaneously. Specifically, the sensitizing antigen is administered to a mammal several times every four to 21 days. The sensitizing antigen is used for immunization after dilution to a suitable dilution ratio with phosphate-buffered saline (PBS), physiological saline, or the like. The sensitizing antigen can also be administered with an adjuvant. For example, it can be mixed with Freund's complete adjuvant and emulsified for use as the sensitizing antigen. A suitable carrier can also be used when immunizing with the sensitizing antigen. In particular, when a partial peptide with a low molecular weight is used as the sensitizing antigen, it is desirable to bind the sensitizing antigen to a carrier protein, such as albumin, keyhole limpet hemocyanin, and the like, for immunization.

After the mammal has been immunized in this manner and it has been confirmed that the level of the desired antibody in the serum has increased, the immune cells are harvested from the mammal and used for cell fusion. In particular, spleen cells can be used preferably as the immune cells.

Mammalian myeloma cells are used as the cells to be fused with the immune cells. The myeloma cells preferably have a suitable selection marker for screening. A selection marker refers to a trait that allows cells to live (or not) under certain culture conditions. Known selection markers include hypoxanthine-guanine phosphoribosyl transferase deficiency (hereinafter abbreviated to "HGPRT deficiency") and thymidine kinase deficiency (hereinafter abbreviated to "TK deficiency"). Cells deficient in HGPRT or TK are hypoxanthine-aminopterin-thymidine sensitive (hereinafter abbreviated to "HAT sensitivity"). HAT-sensitive cells are unable to synthesize DNA and die in HAT selection medium. However, when fused with normal cells, they can continue to synthesize DNA using the salvage pathway of normal cells and therefore they begin to grow in HAT selection medium.

HGPRT-deficient cells and TK-deficient cells can both be selected with a medium containing 6-thioguanine, 8-azaguanine (hereinafter abbreviated to "8AG") or 5'-bromodeoxyuridine. Although normal cells die as a result of incorporating these pyrimidine analogs into their DNA, cells deficient in these enzymes are unable to incorporate these pyrimidine analogs and can thus survive in the selection medium. A selection marker referred to as G418 resistance also imparts resistance to 2-deoxystreptamine-type antibiotics (gentamycin analogs) because it is a neomycin-resistance gene. Various myeloma cells that are suitable for cell fusion are known, and examples of myeloma cells that can be used include P3 (P3x63Ag8.653) (J. Immunol. (1979) 123, 1548-1550), P3x63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), 5194 (Trowbridge, I. S., J. Exp. Med. (1978) 148, 313-323), and R210 cells (Galfre, G. et al., Nature (1979) 277, 131-133).

The fusion of the aforementioned immune cells and myeloma cells can be carried out according to known methods, such as the method of Kohler and Milstein (Kohler, G. and Milstein, C., Methods Enzymol. (1981) 73, 3-46).

More specifically, the aforementioned cell fusion can be carried out in an ordinary nutritive culture medium in the presence of a cell fusion promoter. Examples of cell fusion promoters that can be used include polyethylene glycol (PEG) and Sendai virus (HVJ). An auxiliary agent, such as dimethylsulfoxide, can also be added as desired to further enhance the fusion efficiency.

The ratio in which the immune cells and myeloma cells are used can be set arbitrarily. For example, there are preferably 1-10 times more immune cells than myeloma cells. Examples of culture media that can be used for the cell fusion described above include MEM and RPMI1640 culture medium, preferably used for the growth of the aforementioned myeloma cell lines, as well as ordinary culture medium used for this type of cell culture. A serum supplement, such as fetal calf serum (FCS), can also be added to the culture medium.

Cell fusion is carried out to form target fused cells (hybridomas) by thoroughly mixing predetermined amounts of the immune cells and myeloma cells in the culture medium and then mixing in PEG solution, prewarmed to about 37° C. During cell fusion, PEG, with an average molecular weight of about 1000-6000, for example, can normally be added at a concentration of 30%-60% (w/v). Subsequently, the cell fusion agents and other agents not amenable to hybridoma growth are removed by the repeated sequential addition of a suitable culture medium, as indicated above, centrifugation, and the removal of the supernatant.

The hybridomas thus obtained can be selected with a selective culture medium corresponding to the selection marker possessed by the myeloma used for cell fusion. For example, HGPRT- or TK-deficient cells can be selected by culture in HAT culture medium (culture medium containing hypoxanthine, aminopterin, and thymidine). When HAT-sensitive myeloma cells are used for cell fusion, those cells that have successfully fused with normal cells can be selectively grown in HAT culture medium. Culture in HAT medium is continued for an adequate amount of time for cells other than the target hybridomas (nonfused cells) to die. Specifically, the target hybridomas can generally be selected by culture for several days to several weeks. Next, screening and monocloning for a hybridoma that produces the target antibody can be performed with an ordinary limiting dilution method. Alternatively, an antibody that recognizes AXL can be prepared using the method described in International Publication No. WO 03/104453.

Screening and monocloning for a target antibody is preferably carried out with a known screening method based on an antigen-antibody reaction. For example, an antigen is bound to a carrier, such as polystyrene beads or a commercially available 96-well microtiter plate, and reacted with the culture supernatant of the hybridoma. The carrier is then washed, and reacted with an enzyme-labeled secondary antibody or the like. If a target antibody that reacts with the sensitizing antigen is present in the culture supernatant, the secondary antibody binds to the carrier through this antibody. Finally, whether or not the target antibody is present in the culture supernatant can be determined by detecting the secondary antibody bound to the carrier. A hybridoma producing the desired antibody, which can bind to the antigen, can be cloned by a method such as limiting dilution. At this time, the antigen used for immunization or a substantially equivalent AXL protein can be used preferentially as the antigen.

In addition to the method for producing a hybridoma by immunizing an animal other than a human with an antigen, a target antibody can also be obtained by sensitizing human lymphocytes with the antigen. Specifically, human lymphocytes are first sensitized with AXL protein in vitro. The immunosensitized lymphocytes are then fused to a suitable fusion partner. Myeloma cells of human origin, with the ability to divide continuously, for example, can be used as the fusion partner (see Japanese Patent Application Kokoku Publication No. (JP-B) H1-59878 (examined, approved Japanese patent application published for opposition)). An anti-AXL antibody produced with this method is a human antibody with binding activity for AXL protein.

An anti-AXL human antibody can also be obtained by administering AXL protein as the antigen to a transgenic animal with the entire repertoire of human antibody genes. Antibody-producing cells of the immunized animal can be immortalized by treatments such as fusion with a suitable fusion partner or infection with Epstein-Barr virus. An anti-AXL antibody can also be obtained by isolating a human antibody directed against AXL protein from immortalized cells obtained in this manner (see International Publication Nos WO 94/25585, WO 93/12227, WO 92/03918, and WO 94/02602). Cells producing antibodies with target reaction specificity can also be cloned by cloning the immortalized cells. When using a transgenic animal as the immunized animal, the immune system of the animal recognizes human AXL as foreign. Thus, a human antibody directed against human AXL can easily be obtained. A hybridoma producing a monoclonal antibody prepared in this manner can be subcultured in ordinary culture medium. The hybridoma can also be stored for an extended period of time in liquid nitrogen.

The hybridoma can be cultured in accordance with ordinary methods to obtain the target monoclonal antibody from its culture supernatant. Alternatively, the monoclonal antibody can be produced by administering the hybridoma to a mammal compatible with it to allow the hybridoma to grow, using the resulting ascites as the monoclonal antibody. The former method is suitable for obtaining highly pure antibody.

In the present invention, an antibody encoded by antibody genes cloned from antibody-producing cells can also be used. Cloned antibody genes can be expressed as antibody by incorporating them in a suitable vector and introducing the vector into a host. Methods for isolating the antibody genes, introducing them into a vector, and transforming host cells with it have already been established (see, for example, Vandamme, A. M. et al., Eur. J. Biochem. (1990) 192, 767-775).

For example, a cDNA encoding a variable region (V region) of the anti-AXL antibody can be obtained from hybridoma cells producing the anti-AXL antibody. To accomplish this, total RNA is usually first extracted from the hybridoma. Examples of methods for extracting mRNA from cells include guanidine ultracentrifugation (Chirgwin, J. M. et al., Biochemistry (1979) 18, 5294-5299) and the AGPC method (Chomczynski, P. et al., Anal. Biochem. (1987) 162, 156-159).

The extracted mRNA can be purified using an mRNA Purification Kit (GE Healthcare Bio-sciences) and the like. Alternatively, kits such as the QuickPrep mRNA Purification Kit (GE Healthcare Bio-sciences) are commercially available for the extraction of all mRNAs directly from cells. These kits can be used to obtain all mRNAs from a hybridoma. The cDNA encoding an antibody V region can be synthesized from the resulting mRNAs using reverse transcriptase. The cDNA can be synthesized with, for example, the AMV Reverse Transcriptase First-strand cDNA Synthesis Kit (Seikagaku Corp.). The 5'-Ampli FINDER RACE Kit (Clontech) and 5'-RACE method using PCR (Frohman, M. A. et al., Proc. Natl Acad. Sci. U.S.A. (1988) 85, 8998-9002, Belyavsky, A. et al., Nucleic Acids Res. (1989) 17, 2919-2932) can be used to synthesize and amplify the cDNA. Suitable restriction sites, described below, can also be introduced at both ends of the cDNA during the course of cDNA synthesis.

Target cDNA fragments are purified from the resulting PCR product and linked to vector DNA. A recombinant vector is thus prepared, and after its introduction into *Escherichia coli* or the like and the selection of colonies, the desired recombinant vector can be prepared from the *E. coli* that formed colonies. Whether or not the recombinant vector has the nucleotide sequences of the target cDNA can be confirmed by a known method, such as dideoxynucleotide chain termination sequencing.

PCR using a primer that amplifies a variable region gene can also be used to obtain a gene encoding a variable region. First, cDNA is synthesized using the extracted mRNA as the template to construct a cDNA library. It is convenient to use a commercially available kit to synthesize the cDNA library. Because the amount of mRNA obtained from only a small number of cells is extremely small, its direct purification results in a low yield. Thus, mRNA is normally purified after the addition of a carrier RNA that clearly does not contain any antibody gene. Alternatively, when it is possible to extract a certain amount of RNA, RNA from only antibody-producing cells can be efficiently extracted. For example, the addition of carrier RNA may not be necessary for the extraction of RNA from 10 or more, 30 or more, or preferably 50 or more antibody-producing cells.

The antibody gene is then amplified by PCR using the cDNA library thus constructed as the template. Primers for amplifying the antibody genes by PCR are known. For example, primers to amplify human antibody genes can be designed based on the literature (for example, J. Mol. Biol. (1991) 222, 581-597). These primers have nucleotide sequences that differ for each immunoglobulin subclass. Thus, when a cDNA library of an unknown subclass is used as the template, PCR is performed with all possibilities considered.

For example, when a gene encoding human IgG is to be obtained, primers that amplify a gene encoding γ1 to γ5 as heavy chains and κ and λ chains as light chains can be used. To amplify a variable region gene of IgG, a primer that anneals to a sequence corresponding to the hinge region is typically used for the primer on the 3' side. Conversely, a primer corresponding to each subclass can be used for the primer on the 5' side.

The PCR products amplified with primers that amplify the genes of each subclass of heavy chains and light chains are made into independent libraries. The use of a library synthesized in this manner makes it possible to reconstitute immunoglobulins comprised of combinations of heavy chains and light chains. A target antibody can then be screened for using the binding activity of the reconstituted immunoglobulins to AXL as an indicator.

After a cDNA encoding a V region of the target anti-AXL antibody is obtained, the cDNA is digested with a restriction enzyme that recognizes a restriction site inserted into both ends of the cDNA. A preferred restriction enzyme recognizes and digests a nucleotide sequence that is unlikely to occur in the nucleotide sequence constituting the antibody gene. A restriction enzyme that imparts a cohesive end is preferable when inserting a single copy of the digested fragment into a vector in the proper direction. An antibody expression vector can be generated by inserting the cDNA encoding V regions of the anti-AXL antibody, digested as described above, into a suitable expression vector. At this time, a chimeric antibody can be produced by fusing in frame genes encoding an antibody constant region (C region) and genes encoding the V region described above. Herein, "chimeric antibody" refers to an antibody containing constant and variable regions derived from different organisms. Thus, xenogeneic chimeric antibodies, such as mouse-human antibodies and human-human allogeneic chimeric antibodies, are included in the chimeric antibodies of the present invention. A chimeric antibody expression vector can also be constructed by inserting the V region genes into an expression vector that originally had constant regions.

Specifically, the recognition sequence of a restriction enzyme that digests the V region gene can be arranged on the 5' side of an expression vector retaining a DNA encoding the desired antibody constant region (C region). A chimeric antibody expression vector is constructed by digesting the two with the same combination of restriction enzymes and then fusing them in frame.

Antibody genes can be incorporated into an expression vector for expression under the control of an expression control domain to produce the anti-AXL antibody of the present invention. An expression control domain for expressing antibody can include, for example, an enhancer and a promoter. Recombinant cells expressing DNA encoding the anti-AXL antibody can then be obtained by transforming suitable host cells with this expression vector.

In the expression of antibody genes, DNAs encoding the antibody heavy chain (H chain) and light chain (L chain) can each be incorporated into different expression vectors. Vectors incorporating either the H chain or the L chain can express an antibody molecule with the H chain and L chain after the vectors are simultaneously transformed (cotransfected) into the same host cell. Alternatively, DNAs encoding H chain and L chain can be incorporated in a single expression vector to transform host cells (see International Publication No. WO 94/11523).

Many combinations of hosts and expression vectors are known for the preparation of antibodies by first isolating antibody genes and then introducing them into a suitable host. All of these expression systems can be applied to the present invention. Animal cells, plant cells, or fungal cells can be used when eukaryotic cells are used as hosts. Specific examples of animal cells that can be used in the present invention include mammalian cells (such as CHO, COS, myeloma, BHK [baby hamster kidney], Hela, and Vero cells), amphibian cells (such as *Xenopus* oocytes), and insect cells (such as sf9, sf21, and Tn5 cells).

Known examples of plant cells used in antibody gene expression systems are cells from the genus *Nicotiana*, such as *Nicotiana tabacum*. Callus-cultured cells can be used for plant cell transformation.

Examples of fungal cells that can be used include those of yeast (the genus *Saccharomyces*, such as *Saccharomyces cerevisiae*, and the methanol-utilizing yeast genus *Pichia*, such as *Pichia pastoris*) and of filamentous fungi (the genus *Aspergillus*, such as *Aspergillus niger*).

Antibody gene expression systems that use prokaryotic cells are also known. For example, cells of bacteria such as *E. coli* or *Bacillus subtilis* can be used in the present invention.

When using mammalian cells, an expression vector can be constructed in which a routinely used useful promoter, the antibody genes to be expressed, and a polyA signal at the 3' side downstream from it are operably linked. An example of a promoter/enhancer is human cytomegalovirus immediate early promoter/enhancer.

Other examples of promoter/enhancers that can be used to express an antibody of the present invention include viral promoter/enhancers or mammalian cell promoter/enhancers, such as human elongation factor 1α (HEF1α). Specific examples of viruses whose promoter/enhancers are useful include retroviruses, polyomaviruses, adenoviruses, and simian virus 40 (SV40).

When using an SV40 promoter/enhancer, the method of Mulligan et al. can be used (Nature (1979) 277, 108). An HEF1α promoter/enhancer can also be used to easily express a target gene with the method of Mizushima et al. (Nucleic Acids Res. (1990) 18, 5322).

With *E. coli*, antibody genes can be expressed by operably linking a routinely used useful promoter, an antibody secretion signal sequence, and the antibody genes to be expressed. Examples of promoters include the lacZ promoter and the araB promoter. When using the lacZ promoter, the method of Ward et al. can be used (Nature (1989) 341, 544-546; FASEB J. (1992) 6, 2422-2427). Alternatively, the araB promoter can be used to express target genes according to the method of Better et al. (Science (1988) 240, 1041-1043).

An example of the antibody secretion signal sequence that can be used for the production into the periplasm of *E. coli* is the pelB signal sequence (Lei, S. P. et al., J. Bacteriol. (1987) 169, 4379). The antibody produced in the periplasm is separated and then structurally refolded using a protein denaturant such as a guanidine hydrochloride or urea so that the antibody has the desired binding activity.

Examples of useful replication origins that can be inserted into an expression vector include those originating in SV40, polyomaviruses, adenoviruses, and bovine papillomavirus (BPV). A selection marker can also be inserted into the expression vector to amplify the number of gene copies in a host cell system. Specific examples of selection markers that can be used include the aminoglycoside transferase (APH) gene, the thymidine kinase (TK) gene, the *E. coli* xanthine-guanine phosphoribosyl transferase (Ecogpt) gene, and the dihydrofolate reductase (dhfr) gene.

A target antibody is produced by introducing these expression vectors into host cells and culturing the transformed host cells in vitro or in vivo. Culture of the host cells is carried out in accordance with known methods. Examples of culture media that can be used include DMEM, MEM, RPMI1640, and IMDM, and these can be used in combination with a serum supplement such as FCS.

An antibody expressed and produced in the manner described above can be purified using known methods that are routinely used for protein purification, either alone or in a suitable combination. For example, antibodies can be separated and purified by the suitable selection and combination of, for example, an affinity column such as a Protein A column, a chromatography column, a filter, ultrafiltration, salting out, or dialysis (Antibodies—A Laboratory Manual, Ed Harlow and David Lane, Cold Spring Harbor Laboratory, 1988).

In addition to the host cells described above, a transgenic animal can also be used to produce the recombinant antibody. A target antibody can be obtained from an animal into which a gene encoding the target antibody has been introduced. For example, antibody genes can be constructed as fused genes by inserting them into a gene encoding a protein inherently produced in frame in milk. Goat β casein, for example, can be used as this protein secreted in milk. A DNA fragment containing the fused genes into which the antibody genes have been inserted is injected into a goat embryo and the injected embryo is introduced into a female goat. The desired antibody can be acquired in the form of a fusion protein, fused to milk protein, from milk produced by the transgenic goat (or offspring thereof) born from the goat that received the embryo. Hormones can be given as appropriate to the transgenic goat to increase the amount of milk containing the desired antibody produced by it (Ebert, K. M. et al., Bio/Technology (1994) 12, 699-702). A C region originating in an animal antibody can be used for the C region of a recombinant antibody of the present invention. Examples of useful mouse antibody H chain C regions include Cγ1, Cγ2a, Cγ2b, Cγ3, Cμ, Cδ, Cα1, Cα2, and Cε, and examples of L chain C regions include Cκ and Cλ. Examples of useful animal antibodies other than mouse antibodies include rat, rabbit, goat, sheep, camel, and monkey antibodies. The sequences of these antibodies are known. The C region can also be modified to improve the stability of the antibody or its production. In the present invention, when administering the antibody to a human, an artificially modified recombinant antibody can be made in order to, for example, lower its xenogeneic antigenicity in humans. Examples of recombinant antibodies include chimeric antibodies and humanized antibodies.

These modified antibodies can be produced using known methods. Chimeric antibodies refer to antibodies in which variable regions and constant regions of different origins are linked. For example, an antibody with heavy chain and light chain variable regions of a mouse antibody and heavy chain and light chain constant regions of a human antibody is a mouse-human xenogeneic chimeric antibody. A recombinant vector expressing a chimeric antibody can be prepared by linking DNA encoding variable regions of a mouse antibody with a DNA encoding a constant region of a human antibody and then incorporating it into an expression vector. Recombinant cells transformed with the vector are cultured and the incorporated DNAs are expressed to obtain the chimeric antibody produced in a culture. C regions of a human antibody are used as the C regions of chimeric antibodies and humanized antibodies. For example, Cγ1, Cγ2, Cγ3, Cγ4, Cμ, Cδ, Cα1, Cα2, and Cε can be used for the C region in H chains. Cκ and Cλ can be used for the C region in L chains. The amino acid sequences of these C regions and the nucleotide sequences that encode them are known. A human antibody C region can also be modified to improve the stability of the antibody itself or the antibody production.

In general, chimeric antibodies are composed of V regions originating from antibodies of an animal other than a human and C regions originating from human antibodies. In contrast, humanized antibodies are composed of complementarity determining regions (CDRs) originating from antibodies of animals other than humans, framework regions (FRs) originating from human antibodies, and C regions originating from human antibodies. Because humanized antibodies have reduced antigenicity in the human body, they are useful as an active ingredient of a therapeutic agent of the present invention.

Antibody variable regions are normally composed of three CDRs flanked by four FRs. A CDR is substantially a region that determines the binding specificity of an antibody. The amino acid sequences of CDRs are rich in diversity. Conversely, the amino acid sequences that constitute FRs often demonstrate high homology, even among antibodies with different binding specificities. Consequently, it is generally considered that the binding specificity of a certain antibody can be grafted onto another antibody by grafting the CDRs.

A humanized antibody is also referred to as a "reshaped" human antibody. Specifically, humanized antibodies in which the antibody CDRs of an animal other than a human, such as a mouse, have been grafted onto human antibodies, are known. General genetic recombination techniques for producing humanized antibodies are also known.

A specific example of a known method of grafting the CDRs of a mouse antibody to human FRs is overlap extension PCR. In the overlap extension PCR, a nucleotide sequence encoding a CDR of the mouse antibody to be grafted is added to primers used to synthesize a human antibody FR. Primers are prepared for each of the four FRs. In general, it is considered to be advantageous in terms of maintaining the CDR function to select a human FR with high homology to the mouse FR when grafting a mouse CDR onto a human FR. That is, it is generally preferable to use a human FR with an amino acid sequence with high homology to the amino acid sequence of the FR adjacent to the mouse CDR to be grafted.

The nucleotide sequences to be linked are designed so that they are mutually connected in frame. Human FRs are individually synthesized by specific primer sets. As a result, products are obtained in which a DNA that encodes a mouse CDR has been added to each FR. The nucleotide sequences encoding mouse CDRs of the products are designed to overlap one another. A complementary-strand synthesis reaction is then carried out by mutually annealing the overlapping CDR portions of the products synthesized using the human antibody gene as the template. As a result of this reaction, human FRs are linked through the mouse CDR sequence.

Finally, the full length of a V region gene in which three CDRs and four FRs have been linked is amplified by primers that anneal to its 5' and 3' ends and which have suitable restriction enzyme recognition sequences added. A vector for expressing the humanized antibody can then be prepared by inserting the DNA obtained in the manner described above and DNA encoding a human antibody C region into an expression vector so that they are fused in frame. The humanized antibody is then produced in a culture of cultured cells by introducing the recombinant vector into a host to establish recombinant cells, followed by culturing the recombinant cells and expressing the DNA encoding the humanized antibody (see European Patent Publication No. EP 239400 and International Publication No. WO 96/02576).

FRs of a human antibody can be preferentially selected so that the CDRs form a favorable antigen-binding site when linked through the CDRs, by qualitatively or quantitatively measuring and evaluating its binding activity to the antigen of the humanized antibody prepared in the manner described above. Amino acid residues of the FRs can also be substituted as necessary, so that the CDRs of the reshaped human antibody form a suitable antigen-binding site. For example, an amino acid sequence mutation can be introduced into FRs by applying PCR used to graft the mouse CDRs to the human FRs. Specifically, a mutation of a partial nucleotide sequence can be introduced into a primer that anneals to the FR. A mutated nucleotide sequence is introduced into the FR synthesized with such a primer. A mutant FR sequence with a desired property can be selected by measuring and evaluating the binding activity of the amino-acid-substituted mutant antibody to the antigen, using the method described above (Sato, K. et al., Cancer Res. (1993) 53, 851-856).

Methods for acquiring human antibodies are also known. For example, human lymphocytes are sensitized with the desired antigen or cells expressing the desired antigen in vitro. Next, the desired human antibody with binding activity for the antigen can be acquired by fusing the sensitized lymphocytes to human myeloma cells (see JP-B H1-59878). U266 cells, for example, can be used as the human myeloma cells, to serve as the fusion partner.

A desired human antibody can also be acquired by immunizing with the desired antigen a transgenic animal with the entire repertoire of human antibody genes (see International Publication Nos WO 93/12227, WO 92/03918, WO 94/02602, WO 94/25585, WO 96/34096, and WO 96/33735). Moreover, technologies by which human antibodies can be acquired by panning, using a human antibody library, are also known. For example, the V region of a human antibody can be expressed on the surface of a phage in the form of a single-chain antibody (scFv) using the phage display method, thus allowing the selection of a phage that binds to an antigen. By analyzing the genes of the selected phage, it is possible to determine the DNA sequence encoding the V region of the human antibody that binds to the antigen. After determining the DNA sequence of the scFv that binds to the antigen, the V region sequence is fused in frame to the sequence of the C region of the desired human antibody, and is then inserted into a suitable expression vector to prepare an expression vector. The human antibody can be acquired by introducing the expression vector into the preferred expression cells, as described above, and expressing the gene encoding the human antibody. These methods are already known (International Publication Nos WO 92/01047, WO 92/20791, WO 93/06213, WO 93/11236, WO 93/19172, WO 95/01438, and WO 95/15388).

The antibodies of the present invention include not only bivalent antibodies as represented by IgG, but also monovalent antibodies or polyvalent antibodies as represented by IgM, as long as they bind to the AXL protein. The polyvalent antibodies of the present invention include those with the same antigen-binding sites, and those in which some or all of the antigen-binding sites are different. The antibody of the present invention is not limited to the entire antibody molecule, but may also be a minibody or modified antibody thereof, as long as it binds to the AXL protein.

Minibodies include antibody fragments in which a portion of the whole antibody (such as whole IgG) is deleted. Partial deficiencies in antibody molecules are permitted as long as the ability to bind to the AXL antigen is retained. The antibody fragment of the present invention preferably comprises one or both of the heavy chain variable regions (VH) and light chain variable regions (VL). The amino acid sequences of VH or VL can comprise substitutions, deletions, additions, and/or insertions. Moreover, a portion of one or both of VH and VL can be deleted as long as the ability to bind to the AXL antigen is retained. The variable regions may also be chimerized or humanized. Specific examples of antibody fragments include, for example, Fab, Fab', F(ab')2, and Fv. Specific examples of minibodies include Fab, Fab', F(ab')2, Fv, scFV (single-chain Fv), diabody, sc(Fv)2 (single-chain (Fv)2), etc. Polymers of these antibodies (such as dimers, trimers, tetramers, or polymers) are also included in the minibodies of the present invention.

Antibody fragments can be obtained by producing an antibody fragment by treating the antibody with an enzyme. Known examples of enzymes used to produce antibody fragments include papain, pepsin, plasmin, etc. Alternatively, genes encoding these antibody fragments can be constructed, introduced into an expression vector, and then expressed in suitable host cells (see, for example, Co, M. S. et al., J. Immunol. (1994) 152, 2698-2976; Better, M. and Horwitz, A. H., Methods in Enzymology (1989) 178, 476-496; Plueckthun, A. and Skerra, A., Methods in Enzymology (1989) 178, 476-496; Lamoyi, E., Methods in Enzymology (1989) 121, 652-663; Rousseaux, J. et al., Methods in Enzymology (1989) 121, 663-669; and Bird, R. E. et al., TIBTECH (1991) 9, 132-137).

Digestive enzymes cleave a specific position of an antibody fragment to yield an antibody fragment with a specific structure, as indicated below. An arbitrary portion of an antibody can be deleted by applying genetic engineering techniques to an antibody fragment enzymatically obtained in this manner.

Papain digestion: F(ab)2 or Fab
Pepsin digestion: F(ab')2 or Fab'
Plasmin digestion: Facb "Diabody" refers to bivalent antibody fragments constructed by gene fusion (see Holliger, P. et al., Proc. Natl Acad. Sci. U.S.A. (1993) 90, 6444-6448; EP 404,097; WO 93/11161, etc.). Diabodies are dimers composed of two polypeptide chains. Normally, VL and VH within the same chain of the polypeptide chains that forms a dimer are both bound by linkers. The linkers in a diabody are typically too short to allow the VL and VH to bind to each other. Specifically, the number of amino acid residues that constitute a linker is, for example, about five residues. Thus, the VL and VH encoded in the same polypeptide chain cannot form a single-chain variable region fragment, but instead form a dimer with a different single-chain variable region fragment. As a result, a diabody has two antigen-binding sites.

An scFv is obtained by linking the H chain V region and the L chain V region of an antibody. In an scFv, the H chain V region and L chain V region are linked through a linker, preferably a peptide linker (Huston, J. S. et al., Proc. Natl Acad. Sci. U.S.A. (1988) 85, 5879-5883). The H chain V region and L chain V region in an scFv may be derived from any antibody described as an antibody herein. There is no particular limitation on the peptide linkers that link the V regions. For example, any arbitrary single-chain peptide comprising about three to 25 residues can be used as a linker. The V regions can be linked by, for example, the PCR method described above. To link the V regions using the PCR method, a DNA encoding the entire or desired partial amino acid sequence of the DNA sequence encoding the H chain or the H chain V region of the above antibody, and a DNA sequence encoding the L chain or the L chain V region of the above antibody, are used as templates.

DNA encoding the V regions of the H chain and that encoding L chain are both amplified by the PCR method using pairs of primers with sequences corresponding to the sequences at both ends of the DNA to be amplified. Next, DNA encoding the peptide linker portion is prepared. The DNA encoding the peptide linker can also be synthesized by PCR. Nucleotide sequences that can link the amplification products of each separately synthesized V region are added to the 5' side of the primers used at this time. Next, a PCR reaction is carried out using the "H chain V region DNA", the "peptide linker DNA", and the "L chain V region DNA" together with the primers for the assembly PCR. The primers for the assembly PCR consist of a combination of a primer that anneals to the 5' side of the "H chain V region DNA" and a primer that anneals to the 3' side of the "L chain V region DNA". Therefore, the primers for the assembly PCR consist of a primer set that can amplify the DNA encoding the entire sequence of the scFv to be synthesized. Conversely, nucleotide sequences that can link to each V region DNA are added to the "peptide linker DNA". As a result, these DNAs are linked together and the full length of scFv is finally produced as an amplification product of the primers used for the assembly PCR. Once a DNA encoding an scFv is prepared, an expression vector comprising the DNA and recombinant cells transformed with the expression vector can be acquired with ordinary methods. The scFv can also be acquired by expressing the DNA encoding the scFv in cultures of the resulting recombinant cells.

An sc(Fv)2 is a minibody in which two VHs and two VLs are linked by a linker or such to form a single chain (Hudson, et al., J. Immunol. Methods (1999) 231, 177-189). An sc(Fv)2 can be prepared, for example, by connecting scFvs with a linker.

An sc(Fv)2 is preferably an antibody in which two VHs and two VLs are arranged in the order VH, VL, VH, VL (VH-linker-VL-linker-VH-linker-VL) using the N-terminal side of a single-chain polypeptide as the starting point.

Any arbitrary peptide linker that can be introduced by genetic engineering, a synthetic compound linker (for example, those disclosed in Protein Engineering, (1996) 9(3), 299-305) or such, can be used as the linker to link antibody variable regions. Peptide linkers are preferred in the present invention. There is no particular limitation on the length of the peptide linkers, and the length can be suitably selected by those skilled in the art according to the purpose of use. Normally, the number of amino acid residues constituting a peptide linker ranges from one to 100 amino acids, preferably from three to 50 amino acids, more preferably from five to 30 amino acids, and particularly preferably from 12 to 18 amino acids (for example, 15 amino acids).

The amino acid sequence constituting a peptide linker can be any arbitrary sequence as long as it does not inhibit the binding function of the scFv.

Alternatively, V regions can be linked using a synthetic chemical linker (chemical cross-linking agent). Cross-linking agents ordinarily used to cross-link peptide compounds and such can be used in the present invention. Examples of cross-linking agents that can be used include N-hydroxysuccinimide (NHS), disuccinimidylsuberate (DSS), bis(sulfosuccinimidyl)suberate (BS3), dithiobis(succinimidylpropionate) (DSP), dithiobis(sulfosuccinimidylpropionate) (DTSSP), ethyleneglycol bis(succinimidylsuccinate) (EGS), ethyleneglycol bis(sulfosuccinimidylsuccinate) (sulfo-EGS), disuccinimidyl tartrate (DST), disulfosuccinimidyl tartrate (sulfo-DST), bis[2-(succinimidooxycarbonyloxy) ethyl]sulfone (BSOCOES), and bis[2-(sulfosuccinimidooxycarbonyloxy)ethyl]sulfone (sulfo-BSOCOES).

Normally, three linkers are required when four antibody variable regions are linked. The multiple linkers used may be identical or different. A preferred minibody of the present invention is a diabody or sc(Fv)2. To obtain these minibodies, an antibody is treated with an enzyme such as papain or pepsin to produce antibody fragments. Alternatively, a DNA encoding these antibody fragments is constructed, introduced into an expression vector, and then expressed in suitable host cells (see, for example, Co, M. S. et al., J. Immunol. (1994) 152, 2698-2976; Better, M. and Horwitz, A. H., Methods Enzymol. (1989) 178, 476-496; Plueckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

The antibody of the present invention can also be used as a modified antibody bound to various molecules such as polyethylene glycol (PEG) or cytotoxic substances. Such modified antibodies can be obtained by chemically modifying an antibody of the present invention. Antibody modification methods have already been established in the art.

The antibody of the present invention may also be a bispecific antibody. "Bispecific antibody" refers to an antibody that has variable regions that recognize different epitopes within the same antibody molecule. The epitopes may be present in different molecules or present in the same molecule. In the present invention, a bispecific antibody can have antigen-binding sites that recognize different epitopes on an AXL molecule. Alternatively, a bispecific antibody can recognize AXL via one recognition site and a cytotoxic substance by the other recognition site. These antibodies are also included in the antibodies of the present invention.

A bispecific antibody that recognizes an antigen other than AXL can be combined in the present invention. For example, a bispecific antibody that recognizes an antigen other than AXL, which is specifically expressed on the surfaces of target cancer cells in the same manner as AXL, can be combined.

Methods for producing bispecific antibodies are known. For example, a bispecific antibody can be produced by linking two types of antibodies that recognize different antigens. Each of the linked antibodies may be a half molecule, with the H and L chains, or a quarter molecule comprising only the H chain. Alternatively, fused cells that produce bispecific antibodies can be prepared by fusing hybridomas producing different monoclonal antibodies. Bispecific antibodies can also be prepared with genetic engineering techniques.

Binding Activity of an Antibody

Known means can be used to measure the antigen-binding activity of an antibody (Antibodies A Laboratory Manual, Ed Harlow and David Lane, Cold Spring Harbor Laboratory, 1988). Examples of methods that can be used include ELISA (enzyme-linked immunosorbent assay), EIA (enzyme immunoassay), RIA (radioimmunoassay), fluorescent immunoassay, etc. Examples of the means for measuring the binding activity of an antibody to an antigen expressed in cells include the method described on pages 359-420 of "Antibodies A Laboratory Manual" mentioned above.

Methods using a flow cytometer are particularly preferably used to measure the binding between an antigen expressed on the surface of cells suspended in a buffer and such, and an antibody to that antigen. Examples of flow cytometers used include the FACSCanto™ II, FACSAria™, FACSArray™, FACSVantage™ SE, and FACSCalibur™ (all from BD Biosciences), and the EPICS ALTRA HyPerSort, Cytomics FC 500, EPICS XL-MCL ADC, EPICS XL ADC, and Cell Lab Quanta/Cell Lab Quanta SC (all from Beckman Coulter).

An example of a preferred method of measuring the binding activity of a test AXL antibody to an antigen is the method of staining with a secondary antibody labeled with FITC, which recognizes a test antibody reacted with cells expressing AXL, and then measuring with the FACSCalibur (BD Biosciences) and analyzing the fluorescence intensity using CellQuest software (BD Biosciences).

Hybridomas

The present invention also provides hybridomas deposited under Accession Nos. FERM BP-10858 (AX285), FERM BP-10859 (AX292), FERM BP-10853 (AX223), FERM BP-10852 (AX96), FERM BP-10856 (AX258), FERM BP-10857 (AX284), FERM BP-10850 (Ax7), FERM BP-10851 (Ax51), FERM BP-10854 (Ax225), and FERM BP-10855 (Ax232). These hybridomas produce anti-AXL antibodies with agonistic activity, anti-AXL antibodies with antagonistic activity, anti-AXL antibodies with activity that lowers the expression level of AXL, anti-AXL antibodies with angiogenesis inhibitory activity, and/or anti-AXL antibodies with cell-growth-suppressing activity.

Angiogenesis Inhibitors

The present invention also provides angiogenesis inhibitors comprising an anti-AXL antibody. There is no particular limitation on the mechanism by which angiogenesis is inhibited. Examples of the mechanism include an inhibitory effect on the migration activity of vascular endothelial cells, an apoptosis-inducing action on vascular endothelial cells, and an inhibitory effect on the vascular morphogenesis of vascular endothelial cells. The angiogenesis inhibitors of the present invention preferably inhibit angiogenesis in cancer tissues. There is no particular limitation on the cancer tissues. Examples of these cancer tissues include pancreatic cancer tissues (pancreatic adenocarcinoma tissues, etc.), gastric cancer tissues, lung cancer tissues (tissues of small-cell lung cancer, non-small-cell lung cancer, and such), osteosarcoma tissues, colon cancer tissues, prostate cancer tissues, melanoma tissues, endometrial cancer tissues, ovarian cancer tissues, uterine leiomyosarcoma tissues, thyroid cancer tissues, cancer stem cell tissues, breast cancer tissues, bladder cancer tissues, renal cancer tissues, glioma tissues, neuroblastoma tissues, and esophageal cancer tissues. More preferable tissues are glioma tissue, gastric cancer tissue, endometrial cancer tissue, non-small-cell lung cancer tissue, pancreatic adenocarcinoma tissue, and breast cancer tissue, particularly pancreatic adenocarcinoma tissue and breast cancer tissue.

There is no particular limitation on the antibodies used in the angiogenesis inhibitors of the present invention, as long as they have an angiogenesis inhibitory effect. For example, the antibodies described above (antibodies with agonistic activity, antibodies with antagonistic activity, antibodies with activity that lowers the expression level of AXL, etc.) can be used.

The angiogenesis inhibitors comprising the anti-AXL antibody of the present invention can be expressed as methods for inhibiting angiogenesis using an anti-AXL antibody. The angiogenesis inhibitors comprising the anti-AXL antibody of the present invention can be expressed as use of an anti-AXL antibody for producing an angiogenesis inhibitor.

Cell-Growth Suppressants

The present invention also provides cell-growth suppressants comprising anti-AXL antibodies. There is no particular limitation on the mechanism by which cell growth is suppressed. Examples of the mechanisms include those based on the angiogenesis inhibitory action, those based on the cytotoxic activity of the antibody, and those based on a cytotoxic substance bound to the antibody, but those based on the angiogenesis inhibitory action are preferable.

There is no particular limitation on the cells whose growth is suppressed by an anti-AXL antibody. The cells are preferably those related to a disease, and more preferably cancer cells. Thus, examples of the preferred embodiments of the cell-growth suppressants of the present invention include an anticancer agent comprising an anti-AXL antibody. When the cells are cancer cells, there is no particular limitation on the type of cancer, and the types include pancreatic cancer (pancreatic adenocarcinoma, etc.), gastric cancer, lung cancer (small-cell lung cancer, non-small-cell lung cancer, and such), osteosarcoma, colon cancer, prostate cancer, melanoma, endometrial cancer, ovarian cancer, uterine leiomyosarcoma, thyroid cancer, cancer stem cell, breast cancer, bladder cancer, renal cancer, glioma, neuroblastoma, and esophageal cancer. More preferable cancers are glioma, gastric cancer, endometrial cancer, non-small-cell lung cancer, pancreatic adenocarcinoma, and breast cancer, particularly pancreatic adenocarcinoma and breast cancer.

There is no particular limitation on the antibodies used in the cell-growth suppressants of the present invention, as long as they have cell-growth-suppressing activity. For example, the antibodies described above (antibodies with agonistic activity, antibodies with antagonistic activity, antibodies with activity that lowers the expression level of AXL, etc.) can be used.

The cell-growth suppressants comprising the anti-AXL antibody of the present invention can be expressed as methods for suppressing cell growth using an anti-AXL antibody. When the cells whose growth is suppressed are cancer cells, the anticancer agents comprising the anti-AXL antibody of the present invention can be expressed as methods for treating and/or preventing cancer using an anti-AXL antibody. The cell-growth suppressants comprising the anti-AXL antibody of the present invention can be expressed as use of an anti-AXL antibody to produce a cell-growth suppressant. When the cells whose growth is suppressed are cancer cells, they can be expressed as use of an anti-AXL antibody for producing an anticancer agent.

Phosphorylation Inducers

The present invention also provides phosphorylation inducers comprising an anti-AXL antibody. The phosphorylation inducers of the present invention normally induce phosphorylation in cells expressing AXL. Although there is no particular limitation on the targets of the phosphorylation induction, the targets are normally polypeptides having tyrosine and are preferably AXL.

There is no particular limitation on the antibodies used in the phosphorylation inducers of the present invention. For example, the antibodies with agonistic activity described above can be used.

The phosphorylation inducers comprising the anti-AXL antibody of the present invention can be expressed as methods for inducing phosphorylation using an anti-AXL antibody. The phosphorylation inducers comprising the anti-AXL antibody of the present invention can also be expressed as use of an anti-AXL antibody for producing a phosphorylation inducer.

Phosphorylation Inhibitors

The present invention also provides phosphorylation inhibitors comprising an anti-AXL antibody. The phosphorylation inhibitors of the present invention normally inhibit the phosphorylation induced by the binding of an AXL ligand (such as Gas6) to AXL. Although there is no particular limitation on the targets of phosphorylation inhibition, the targets are normally polypeptides having tyrosine and are preferably AXL.

There is no particular limitation on the antibodies used in the phosphorylation inhibitors of the present invention. For example, the antibodies with antagonistic activity described above can be used.

The phosphorylation inhibitors comprising the anti-AXL antibody of the present invention can be expressed as methods for inhibiting phosphorylation using an anti-AXL antibody. The phosphorylation inhibitors comprising the anti-AXL antibody of the present invention can also be expressed as use of an anti-AXL antibody for producing a phosphorylation inhibitor.

Agents for Lowering the AXL Expression Level

The present invention also provides agents that lower the AXL expression level comprising an anti-AXL antibody. The agent that lowers the AXL expression level reduces AXL expression level in cells expressing AXL. There is no particular limitation on the cells that express AXL. Examples of these cells include cancer cells (Calu-1, MDA-MB-231, DU-145, etc.).

The reduction in the expression level of AXL may be a reduction in the amount of AXL already present by the degradation of AXL, or such, or may be a reduction in the amount of newly expressed AXL by suppressing the expression of AXL.

The agents that lower the AXL expression level comprising the anti-AXL antibody of the present invention can be expressed as methods for lowering the expression level of AXL using an anti-AXL antibody. Moreover, the agents that lower the AXL expression level comprising the anti-AXL antibody of the present invention can be expressed as use of an anti-AXL antibody for producing an agent for lowering the AXL expression level.

Pharmaceutical Compositions

The angiogenesis inhibitors, cell-growth suppressants, phosphorylation inducers, phosphorylation inhibitors, or agents that lower the AXL expression level of the present invention can be administered by either oral administration methods or parenteral administration methods. Parenteral administration methods are particularly preferred. Specific examples of such administration methods include injection administration, transnasal administration, transpulmonary administration, and transcutaneous administration. The pharmaceutical compositions of the present invention can be administered systemically or locally by injection administration, for example, by intravenous injection, intramuscular injection, intraperitoneal injection, subcutaneous injection, or such. Suitable methods of administration can also be selected according to the age and symptoms of the patient. The dosage can be selected, for example, within the range of 0.0001 mg to 1000 mg per kilogram body weight per administration. Alternatively, the dosage can be selected, for example, within the range of 0.001 to 100,000 mg/body per patient. However, the dosage of the pharmaceutical compositions of the present invention is not limited thereto.

The angiogenesis inhibitors, cell-growth suppressants, phosphorylation inducers, phosphorylation inhibitors, or agents for lowering the AXL expression level of the present invention can be formulated according to ordinary methods (for example, Remington's Pharmaceutical Science, latest edition, Mark Publishing Company, Easton, USA), and may comprise pharmaceutically acceptable carriers or additives. Examples of the carriers and additives include, but are not limited to, surfactants, vehicles, colorants, fragrances, preservatives, stabilizers, buffers, suspension agents, isotonic agents, binders, disintegration agents, lubricants, fluidity promoters, and flavoring agents. Other commonly used carriers can be used as appropriate. Specific examples of such carriers include light silicic anhydride, lactose, crystalline cellulose, mannitol, starch, carmellose calcium, carmellose sodium, hydroxypropyl cellulose, hydroxypropyl methyl cellulose, polyvinylacetal diethylaminoacetate, polyvinylpyrrolidone, gelatin, medium-chain fatty-acid triglycerides, polyoxyethylene hydrogenated castor oil 60, saccharose, carboxymethyl cellulose, cornstarch, inorganic salts, etc.

All prior art reference cited herein are incorporated by reference in their entirety.

EXAMPLES

Although the present invention will be explained in more detail by the following Examples, the present invention is not limited by these Examples.

Example 1

1-1 Preparation of Antigen

Hamster ovary cells (CHO (dhfr⁻) cells) were transfected with the expression vector for a fusion protein (hAXL-ECD-mIgG2aFc), in which the extracellular domain of human AXL and an Fc domain of mouse IgG2a were fused, and CHO cell lines that produce hAXL-ECD-mIgG2aFc protein were cloned with G418 selection. The culture supernatant of the hAXL-ECD-mIgG2aFc protein-producing CHO cell lines collected using serum-free medium (CHO-S-SFM II; Gibco) was added to a Protein G Column (HiTrap Protein G HP, GE Healthcare) equilibrated with a binding buffer (20 mM phosphate buffer, pH 7.0). After the unbound proteins were washed with the binding buffer, fractions of hAXL-ECD-mIgG2aFc protein were collected with an elution buffer (100 mM glycine-HCl, pH 2.7) into tubes containing neutralizing buffer (1 M Tris-HCl, pH 9.0). Then the buffer of the purified protein was replaced with phosphate-buffered physiological saline (pH 7.35-7.65; Takara Bio) and the purified protein was concentrated using an ultrafiltration kit for a molecular weight fraction of 10 kDa (Centricon (registered trademark), Millipore). The concentration of the purified protein was calculated from the absorbance at 280 nm using a molar absorption coefficient calculated according to the calculation formula of Pace et al. (Prof. Sci. (1995) 4, 2411-2423).

1-2 Preparation of Anti-AXL-Antibody-Producing Hybridoma

Four BALB/c mice (male, six weeks old at the start of immunization, Charles River Laboratories Japan) and two MRL/lpr mice (male, six weeks old at the start of immunization, Charles River Laboratories Japan) were immunized as described below with the antigen prepared in the previous section (hAXL-ECD-mIgG2aFc protein). Antigen emulsified with Freund's complete adjuvant (H37 Ra, Difco Laboratories) was administered subcutaneously at 40 µg/head as the initial immunization. Two weeks later, antigen emulsified with Freund's incomplete adjuvant (Difco Laboratories) was administered subcutaneously at 40 µg/head. The animals were subsequently immunized three times more at one week intervals. Increases in the serum antibody titer in response to the antigen were confirmed by ELISA as indicated in the following section, followed by a final immunization of intravenous administration of antigen diluted with phosphate-buffered physiological saline (phosphate-buffered saline without calcium ions or magnesium ions, PBS(–); Nissui Pharmaceutical) at 10 µg/head. Three days after the final immunization, mouse spleen cells and mouse myeloma cells P3X63Ag8U.1 (referred to as P3U1, ATCC CRL-1597) were fused according to ordinary methods using PEG 1500 (Roche Diagnostics). The fused cells were cultured in RPMI1640 medium (Invitrogen) containing 10% FBS (Invitrogen) (hereafter referred to as 10% FBS/RPMI1640). On the day after fusion, the fused cells were suspended in semifluid medium (StemCells) followed by the selective culture and colonization of the hybridomas. Hybridoma colonies were picked from the medium on the ninth or tenth day after fusion and seeded into a 96-well plate containing HAT selective medium (10% FBS/RPMI1640, 2 vol % HAT 50× concentrate [Dainippon Pharmaceutical] and 5 vol % BM-Condimed H1 [Roche Diagnostics]) at one colony per well. After culture for three to four days, the supernatant was collected from each well and the hybridomas with binding activity to the extracellular domain of human AXL were selected by measuring their binding activity to the aforementioned antigen and to a control protein fused with the Fc domain of mouse IgG2a by ELISA, as indicated in the following section.

The binding activities of the supernatants of the selected hybridomas are shown in Table 1.

TABLE 1

| AXL Clone No. | 2nd SC Abs AXL-mFc | 2nd SC Abs FGFR2-mFc | 2nd SC Abs AbsΔ | 2nd SC Abs AXL-His | IgG Binding |
|---|---|---|---|---|---|
| 7 | 2.053 | 0.057 | 1.996 | 1.118 | 0.66 |
| 51 | 1.844 | 0.058 | 1.786 | 0.538 | 0.55 |
| 232 | 1.353 | 0.061 | 1.292 | 1.204 | 0.575 |
| 96 | 2.122 | 0.058 | 2.064 | 1.554 | 0.635 |
| 119 | 2.208 | 0.063 | 2.145 | 1.527 | 0.668 |
| 223 | 2.076 | 0.071 | 2.005 | 1.542 | 0.339 |
| 225 | 0.629 | 0.055 | 0.574 | 0.642 | 0.859 |
| 258 | 2.005 | 0.078 | 1.927 | 1.028 | 0.74 |
| 284 | 0.619 | 0.064 | 0.555 | 0.124 | 0.857 |
| 285 | 1.804 | 0.058 | 1.746 | 0.914 | 0.965 |
| 292 | 1.877 | 0.069 | 1.808 | 1.234 | 1.052 |

The hybridomas selected by the present inventors were deposited at the International Patent Organism Depositary of the National Institute of Advanced Industrial Science and Technology. The following section provides a description of the contents, specifying the deposition.
(a) Name and Address of the Depositary Institution
Name: International Patent Organism Depositary, National Institute of Advanced Industrial Science and Technology
Address: Tsukuba Central 6, 1-1-1 Higashi, Tsukuba, Ibaraki, Japan 305-8566
(b) Acceptance Date (Deposition Date): Jul. 5, 2007
(c) Accession No.
AXL No. 7 #070402 (Ax7) (Accession No. FERM BP-10850)
AXL No. 51 #070406 (Ax51) (Accession No. FERM BP-10851)
AXL No. 232 #070406 (Ax232) (Accession No. FERM BP-10855)
AXL No. 96 #070402 (Ax96) (Accession No. FERM BP-10852)
AXL No. 223 #070402 (Ax223) (Accession No. FERM BP-10853)
AXL No. 225 #070402 (Ax225) (Accession No. FERM BP-10854)
AXL No. 258 #070402 (Ax258) (Accession No. FERM BP-10856)
AXL No. 284 #070402 (Ax284) (Accession No. FERM BP-10857)
AXL No. 285 #070402 (Ax285) (Accession No. FERM BP-10858)
AXL No. 292 #070411 (Ax292) (Accession No. FERM BP-10859)

1-3 Binding Activity to Human AXL

Antigen (hAXL-ECD-mIgG2aFc) diluted to 1 µg/mL with coating buffer (100 mM sodium bicarbonate [pH 9.6], 0.02% sodium azide) or control protein fused with the Fc domain of mouse IgG2a was dispensed into a 96-well plate (Nunc- Immuno™ 96 MicroWell™ MaxiSorp™ plate; Nalge Nunc International) at 80 µL/well, followed by incubation at least overnight at 4° C. After it was washed three times with phosphate-buffered saline containing 0.05 vol % Tween (registered trademark) 20 (tPBS[−]), the plate was blocked at least overnight at 4° C. with diluent buffer (1/5 dilution of BlockingOne; Nacalai Tesque). After the removal of the buffer, mouse antiserum or hybridoma culture supernatant diluted with diluent buffer was added to the plate at 80 µL/well, followed by incubation for one hour at room temperature. After the plate had been washed three times with tPBS(−), HRP-labeled anti-mouse IgG antibody (Stressgen), diluted 1/5000 with diluent buffer, was added at 80 µL/well, followed by incubation for one hour at room temperature. After the plate had been washed five times with tPBS(−), a chromogenic substrate, Peroxidase Substrate (Kirkegaad & Perry Laboratories), was added at 80 µL/well, followed by incubation for 20 minutes at room temperature. After the addition of Peroxidase Stop Solution (Kirkegaad & Perry Laboratories) at 80 µL/well, the absorbance at 405 nm was measured with a Microplate Reader Model 3550 (Bio-Rad Laboratories).

1-4 Purification of Antibody from Hybridoma Culture Supernatant

The resulting hybridomas described above were cultured in HAT selective medium using low-IgG FBS (Invitrogen) as the FBS. Protein G beads (Pharmacia), in which the solvent was replaced with wash buffer (20 mM sodium acetate buffer, pH 5.0), were added to 20-50 mL of the culture supernatant at 50 µL per 10 mL of culture supernatant, followed by mixing by inversion overnight at 4° C. After the Protein G beads had been retrieved and washed with wash buffer, the antibody was eluted with elution buffer (50 mM sodium acetate buffer, pH 3.3), followed immediately by neutralization with neutralizing buffer (Tris-HCl buffer, pH 7.8). The buffer was replaced with phosphate-buffered physiological saline (pH 7.35-7.65; Nissui Pharmaceutical) and the purified antibody was concentrated using an ultrafiltration kit for a molecular weight fraction of 10 kDa (Amicon (registered trademark), Millipore), followed by sterilization with a 0.22 µm sterilization filter (Millipore GV, Millipore).

Example 2

Assay of Antibody-Induced Phosphorylation

The ability of the anti-AXL monoclonal antibody obtained in Example 1 to induce the phosphorylation of AXL in cancer cells was tested. Cells (human non-small-cell lung cancer cell line Calu-1, human breast cancer cell line MDA-MB-231, and human prostate cancer cell line DU-145) were seeded into six-well plates at a density of $4\times10^5$ cells/well and 24 hours later, the medium was replaced with medium from which the serum had been removed (serum-starved medium) and the cells were cultured overnight. Next, the above-prepared anti-AXL monoclonal antibody was added at 2 µg/mL, and recombinant GAS6 (R&D) was added at 200 ng/mL to act as the positive control, followed by incubation for 30 minutes at 37° C. Next, the cells were washed with PBS(−) and lysed on ice for 30 minutes with cell lysis buffer (137 mM NaCl, 20 mM Tris-HCl [pH 8.0], 10% glycerol, 2 mM EDTA, 1 mM sodium vanadate, 1 vol % NP-40, 1 mM phenylmethylsulfonyl fluoride [PMSF], 10 µg/mL aprotinin, 10 µg/mL leupeptin, 10 µg/mL pepstatin). The cell solution mixture was homogenized with an ultrasonic homogenizer (Tomy Seiko) followed by centrifugation (20,000×g) for 10 minutes at 4° C. The supernatant of the cell solution mixture was mixed for 30 minutes with 0.05 volumes of Protein G Agarose (Roche Diagnostics). After centrifugation (2,300×g) for one minute at 4° C., 1.2 µg of anti-AXL monoclonal antibody (R&D) was added to the supernatant, which was shaken for one hour at 4° C. Then, 10 µL of Protein G Agarose was added and the solution was shaken for a further one hour at 4° C. After centrifugation (2,300 µg) for one minute at 4° C., the immunoprecipitate was washed and suspended in NuPAGE-LDS sample buffer (Invitrogen), and then heated for 10 minutes at 70° C. The immunoprecipitate was electrophoresed for one hour at 150 V using 7% NuPAGE (Invitrogen).

After immunoprecipitation and electrophoresis on 7% NuPAGE, the protein was electrophoretically transferred to a 0.45 µm polyvinylidene difluoride filter (Immobilon-FL, Millipore) over the course of one hour at 30 mA with NuPAGE transfer buffer (Invitrogen) and the buffer containing 20 vol % methanol. The filter was washed with TBS (50 mM Tris-HCl [pH 7.6], 150 mM NaCl) and then blocked by incubation overnight in Odyssey blocking buffer (Li-COR). The filter was washed four times for five minutes each with TBST (TBS containing 0.05 vol % Tween (registered trademark) 20) and then incubated for two hours at room temperature with biotinylated 4G10 anti-phosphotyrosine antibody (diluted 1:1,000 with TBST; Upstate) and anti-AXL antibody (diluted 1:15,000 with TBST; Santa Cruz). After the filter had been washed four times for five minutes each with TBST, the filter was incubated for one hour with Alexa 680-labeled streptavidin (Invitrogen) diluted 1:10,000 with TBST and IRDye 800-labeled anti-goat secondary antibody (Rockland) diluted 1:10,000 with TBST. After the filter had been washed three times for five minutes each with TBST, it was washed again once for five minutes with TBS, and then scanned with the Odyssey infrared imaging system (Li-COR).

A band obtained by immunoblotting the immunoprecipitated intracellular AXL with anti-AXL antibody and a band obtained by immunoblotting it with anti-phosphotyrosine antibody overlapped, and the intensification of the band for tyrosine-phosphorylated AXL was observed after the addition of the anti-AXL monoclonal antibodies Ax285, Ax292, Ax223, Ax96, and Ax258, and after the addition of the recombinant GAS6 used as the positive control (FIGS. 1a, b, c, d, and e). Thus, intensified tyrosine phosphorylation of AXL was observed as a result of the addition of the anti-AXL monoclonal antibody acquired by the present inventors. Thus, these anti-AXL monoclonal antibodies can induce the phosphorylation of the kinase domain of AXL.

Example 3

Assay of the Inhibition of Ligand-Dependent Phosphorylation by the Antibody

Figure 2A:
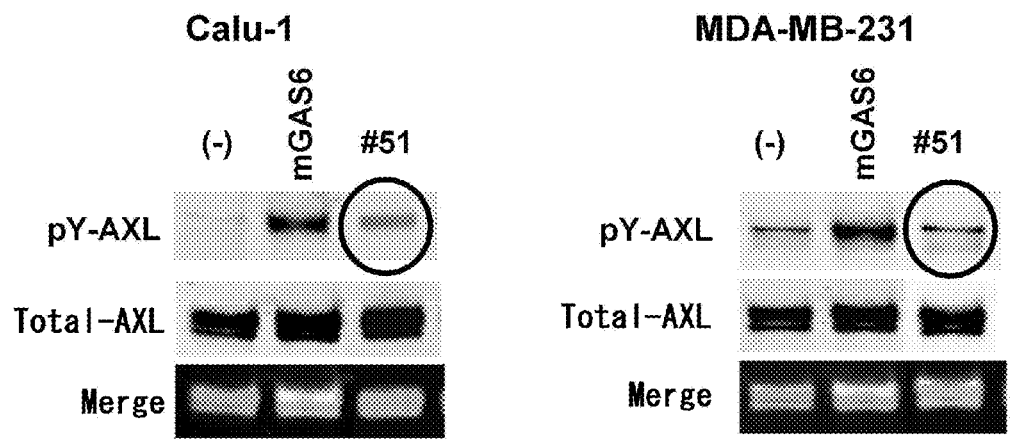
FIG. 2A is a photograph showing the activity of an anti-AXL monoclonal antibody (Ax51) of the present invention, in inhibiting ligand-dependent phosphorylation of AXL in a cell. The antibody was shown to inhibit the ligand-dependent phosphorylation of a kinase domain of AXL.
Figure 2B:
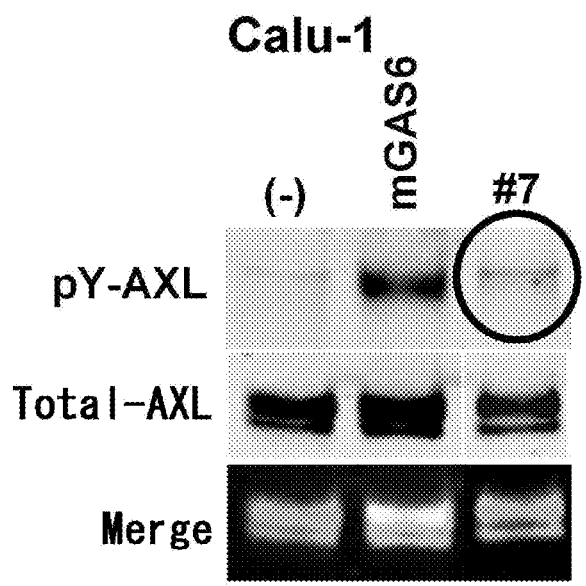
FIG. 2B is a photograph showing the activity of an anti-AXL monoclonal antibody (Ax7) of the present invention, in inhibiting ligand-dependent phosphorylation of AXL in a cell. The antibody was shown to inhibit the ligand-dependent phosphorylation of a kinase domain of AXL.

The ability of the anti-AXL monoclonal antibody to inhibit ligand-dependent phosphorylation within cancer cells was tested. Cells (human non-small-cell lung cancer cell line Calu-1, human breast cancer cell line MDA-MB-231, or human prostate cancer cell line DU-145) were seeded into six-well plates at a density of $4\times10^5$ cells/well and 24 hours later, the medium was replaced with medium from which the serum had been removed (serum-starved medium) and then the cells were cultured overnight. Next, the anti-AXL monoclonal antibody prepared in Example 1 was added at 2 µg/mL, and then recombinant GAS6 (R&D) was added simultaneously at 200 ng/mL and incubated for 30 minutes at 37° C. Next, the cells were washed with PBS(−) and the protein was extracted from the cells with the previously described cell lysis buffer. The cell lysis products, immunoprecipitated with commercially available anti-AXL antibody (Santa Cruz™), were separated on 7% NuPAGE (Invitrogen), immunoblotted by western blotting, and tyrosine phosphorylation assay, as previously described. The immunoprecipitated intracellular AXL was blotted with anti-phosphotyrosine antibody by treatment with GAS6, which is its ligand. However, the blot of the anti-phosphotyrosine antibody was weakened by the anti-AXL monoclonal antibodies Ax7 and Ax51 (FIGS. 2a and b). Thus, the ligand-dependent tyrosine phosphorylation of AXL was confirmed to be inhibited by exposing to the anti-AXL monoclonal antibodies acquired by the present inventors. These anti-AXL monoclonal antibodies can inhibit ligand-dependent phosphorylation of the kinase domain of AXL.

Example 4

Assay of the Induction of AXL Protein Downmodulation by the Antibody

The ability of the anti-AXL monoclonal antibody to induce the downmodulation of AXL within cancer cells was tested. Cells (human non-small-cell lung cancer cell line Calu-1, human breast cancer cell line MDA-MB-231, or human prostate cancer cell line DU-145) were seeded into six-well plates at a density of $4 \times 10^5$ cells/well and 24 hours later, the medium was replaced with medium from which the serum had been removed (serum-starved medium) and then the cells were cultured overnight. Next, the anti-AXL monoclonal antibody prepared as described above was added at 2 µg/mL, and recombinant GAS6 (R&D) was added at 200 ng/mL to act as the positive control, followed by incubation for 24 hours at 37° C. Next, the cells were washed with PBS(–) and the protein was extracted from the cells with the previously described cell lysis buffer. The cell lysis products, immunoprecipitated with a commercially available anti-AXL antibody (Santa Cruz™), were separated on 7% NuPAGE (Invitrogen), immunoblotted by western blotting, and tyrosine phosphorylation assay, as previously described.

25 µg of each protein solution was suspended in NuPAGE-LDS sample buffer (Invitrogen), heated for 10 minutes at 70° C., and electrophoresed for one hour at 150 V on 7% NuPAGE (Invitrogen). The gels separated by electrophoresis were electrophoretically transferred to a 0.45 µm polyvinylidene difluoride filter (Immobilon-FL, Millipore) over the course of one hour at 30 mA in NuPAGE transfer buffer (Invitrogen) and the buffer containing 20 vol % methanol. The filter was washed with TBS (50 mM Tris-HCl [pH 7.6], 150 mM NaCl) and then blocked by incubation overnight in Odyssey blocking buffer (Li-COR). The filter was washed four times for five minutes each with TBST and then incubated for two hours at room temperature with anti-AXL antibody (diluted 1:15,000 with TBST; Santa Cruz) and anti-actin antibody (diluted 1:5,000 with TBST). After the filter had been washed four times for five minutes each with TBST, it was incubated for one hour with Alexa 680-labeled anti-rabbit secondary antibody (Invitrogen) diluted 1:10,000 with TBST and IRDye 800-labeled anti-goat secondary antibody (Rockland) diluted 1:10,000 with TBST. After it had been washed three times for five minutes each with TBST, the filter was washed again once for five minutes with TBS, and then scanned with the Odyssey infrared imaging system (Li-COR).

Figure 3A:
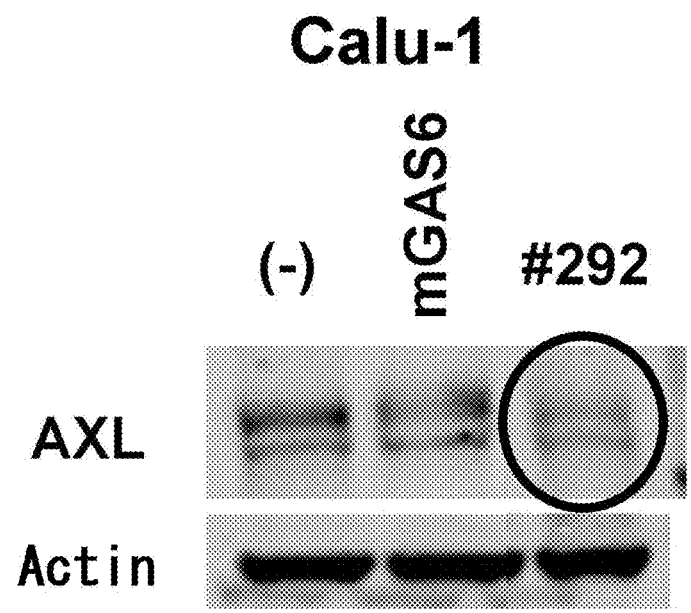
FIG. 3A is a photograph showing the activity of an anti-AXL monoclonal antibody (Ax292) of the present invention, in inducing AXL downmodulation in cancer cells. The antibody was shown to induce the downmodulation of AXL protein.
Figure 3B:
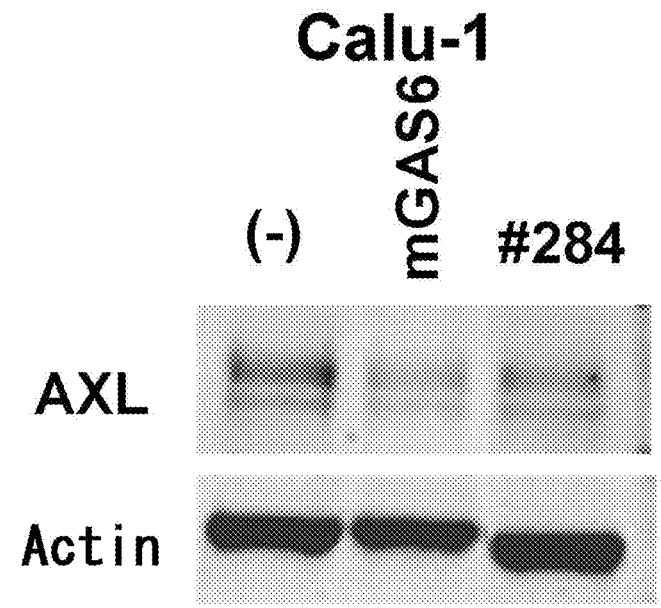
FIG. 3B is a photograph showing the activity of an anti-AXL monoclonal antibody (Ax284) of the present invention, in inducing AXL downmodulation in cancer cells. The antibody was shown to induce the downmodulation of AXL protein.
Figure 3C:
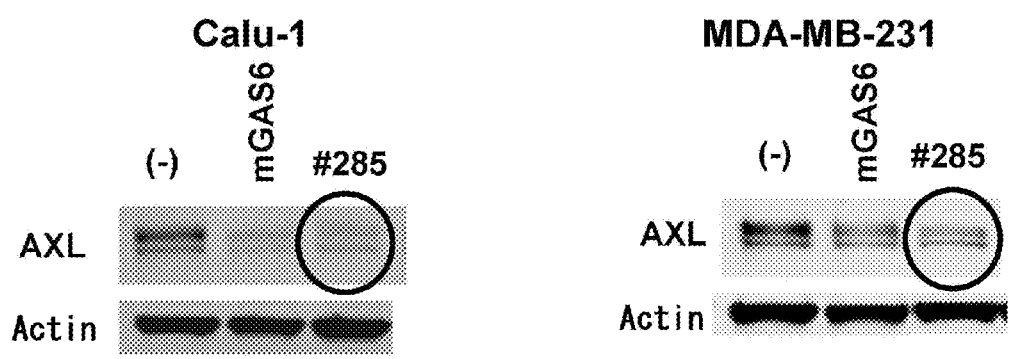
FIG. 3C is a photograph showing the activity of an anti-AXL monoclonal antibody (Ax285) of the present invention, in inducing AXL downmodulation in cancer cells. The antibody was shown to induce the downmodulation of AXL protein.
Figure 3D:
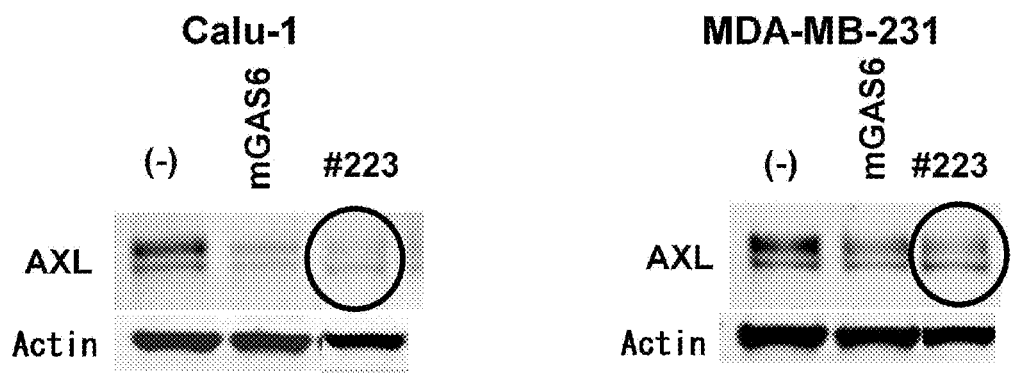
FIG. 3D is a photograph showing the activity of an anti-AXL monoclonal antibody (Ax223) of the present invention, in inducing AXL downmodulation in cancer cells. The antibody was shown to induce the downmodulation of AXL protein.
Figure 3E:
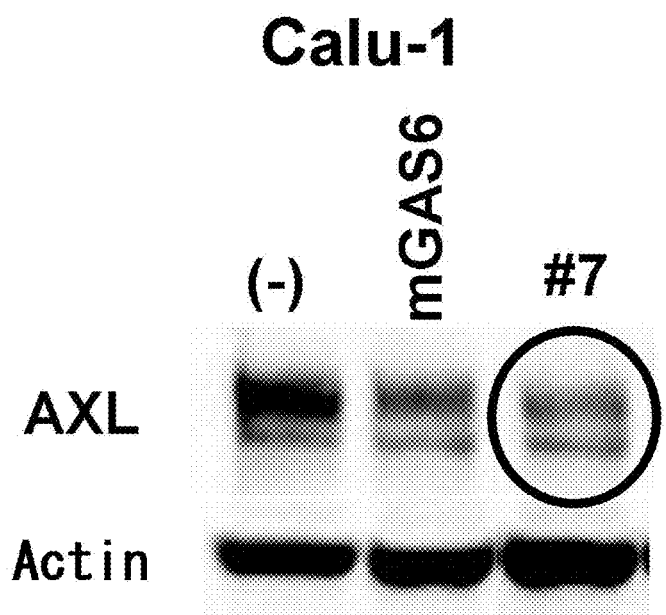
FIG. 3E is a photograph showing the activity of an anti-AXL monoclonal antibody (Ax7) of the present invention, in inducing AXL downmodulation in cancer cells. The antibody was shown to induce the downmodulation of AXL protein.
Figure 3F:
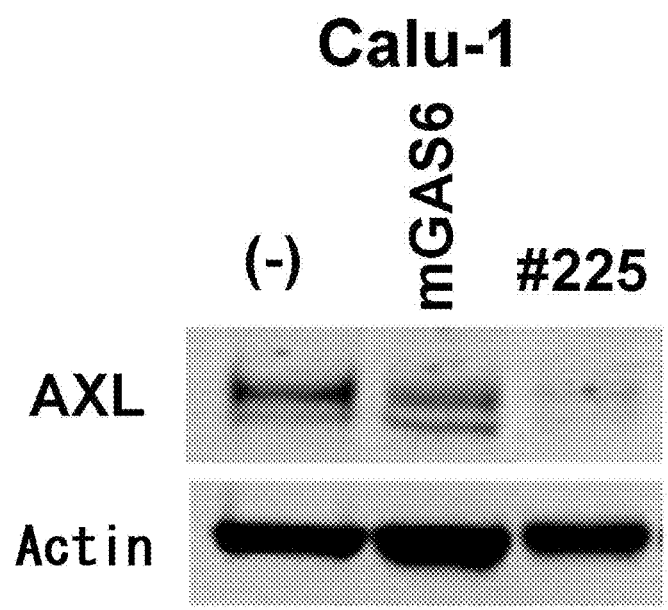
FIG. 3F is a photograph showing the activity of an anti-AXL monoclonal antibody (Ax225) of the present invention, in inducing AXL downmodulation in cancer cells. The antibody was shown to induce the downmodulation of AXL protein.
Figure 3G:
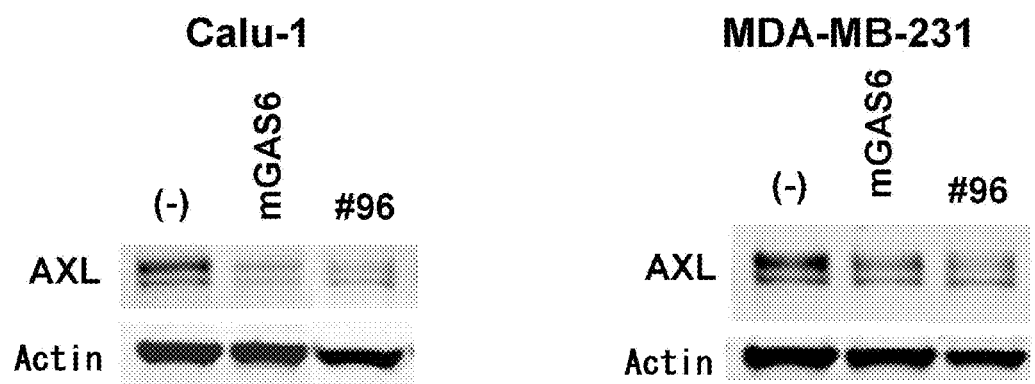
FIG. 3G is a photograph showing the activity of an anti-AXL monoclonal antibody (Ax96) of the present invention, in inducing AXL downmodulation in cancer cells. The antibody was shown to induce the downmodulation of AXL protein.
Figure 3H:
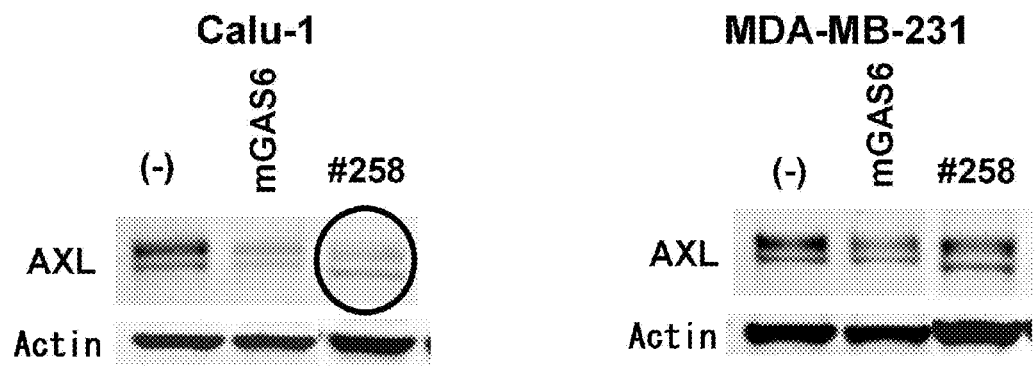
FIG. 3H is a photograph showing the activity of an anti-AXL monoclonal antibody (Ax258) of the present invention, in inducing AXL downmodulation in cancer cells. The antibody was shown to induce the downmodulation of AXL protein.

The AXL blots were observed to weaken following exposure to the anti-AXL monoclonal antibodies Ax285, Ax292, Ax223, Ax96, Ax258, Ax284, Ax7, and Ax225 (FIGS. 3a, b, c, d, e, f, g, and h). Therefore, these anti-AXL monoclonal antibodies can induce the downmodulation of AXL protein.

Example 5

In Vitro Angiogenesis Inhibitory Activity of Anti-AXL Antibody

The activity of anti-AXL antibody to inhibit the lumen formation of human umbilical vein endothelial cells (HUVEC) was measured using an angiogenesis kit available from Kurabo Industries. The experimental procedure was in accordance with the protocol provided with the kit and is summarized below. HUVEC and fibroblasts were cocultured, and a 24-well plate (provided with the kit) containing cells in the growth state of early lumen formation was placed in an incubator for three hours at 37° C. under 5% $CO_2$ and humidified air. The caps of three containers containing 25 mL of special-purpose medium (provided with the kit) were loosened and placed in the incubator for about 30 minutes at 37° C. under 5% $CO_2$ and humidified air. The plate was then removed from the incubator and the well cap sheet was peeled off. The plate cover was then replaced with a new one (provided with the kit). The cells were confirmed to be normal by observation under a microscope. Culture medium (>12 mL/plate), warmed to 37° C., was dispensed into Falcon tubes and VEGF-A (2 µg/mL) was added to the medium to a final concentration of 10 ng/mL by 200-fold dilution. The anti-AXL antibody prepared as described above was added to the medium dispensed into the tubes to a final concentration of 10 µg/mL. PBS(–) was used in place of antibody for the negative control. The medium in the wells of the 24-well plate was gently removed by aspiration and 500 µL of drug-containing medium was then gently added. The condition of the cells was observed microscopically and they were then returned to the incubator. The medium was replaced using the same procedure on days 4, 7, and 9, counting the day on which the antibody was added as day 1.

The cell layer was fixed and stained using a lumen staining kit (Kurabo) on the 11th day after the addition of the antibody. The procedure was carried out according to the protocol provided with the kit and is summarized below. After the cells were observed under a microscope, the medium was removed by aspiration and the well was washed by the addition of 1 mL of wash buffer (PBS(–) pH 7.4; Sigma) to each well, and then the wash buffer was removed by aspiration. 1 mL of ice-cold fixing solution (70% ethanol) was added to each well and allowed to stand for 30 minutes at room temperature. The fixing solution was then removed, 1 mL of blocking solution was added to each well, the well was washed, and the blocking solution was removed by aspiration. 0.5 mL of the primary antibody provided with the kit was diluted according to the protocol and added to each well, followed by incubation for one hour at 37° C. The primary antibody was removed by aspiration and each well was washed three times with 1 mL of blocking solution (PBS(–) containing 1% BSA, pH 7.4; Sigma). 0.5 mL of the secondary antibody provided with the kit and diluted in accordance with the protocol was added to each well, followed by incubation for one hour at 37° C. The secondary antibody was removed by aspiration and each well was washed three times with 1 mL of distilled water. 0.5 mL of the substrate solution provided with the kit was added to each well, followed by incubation for 10-30 minutes at 37° C. until the lumen became dark purple. The substrate solution was then removed by aspiration and each well was washed three times with 1 mL of distilled water and allowed to air dry. Microscopic images of each fixed well were captured at five locations with a CCD camera (Nikon Digital Camera, dxm1200), and the vessel areas were calculated using angiogenesis quantification software (Ver. 1.0, Kurabo).

Figure 4:
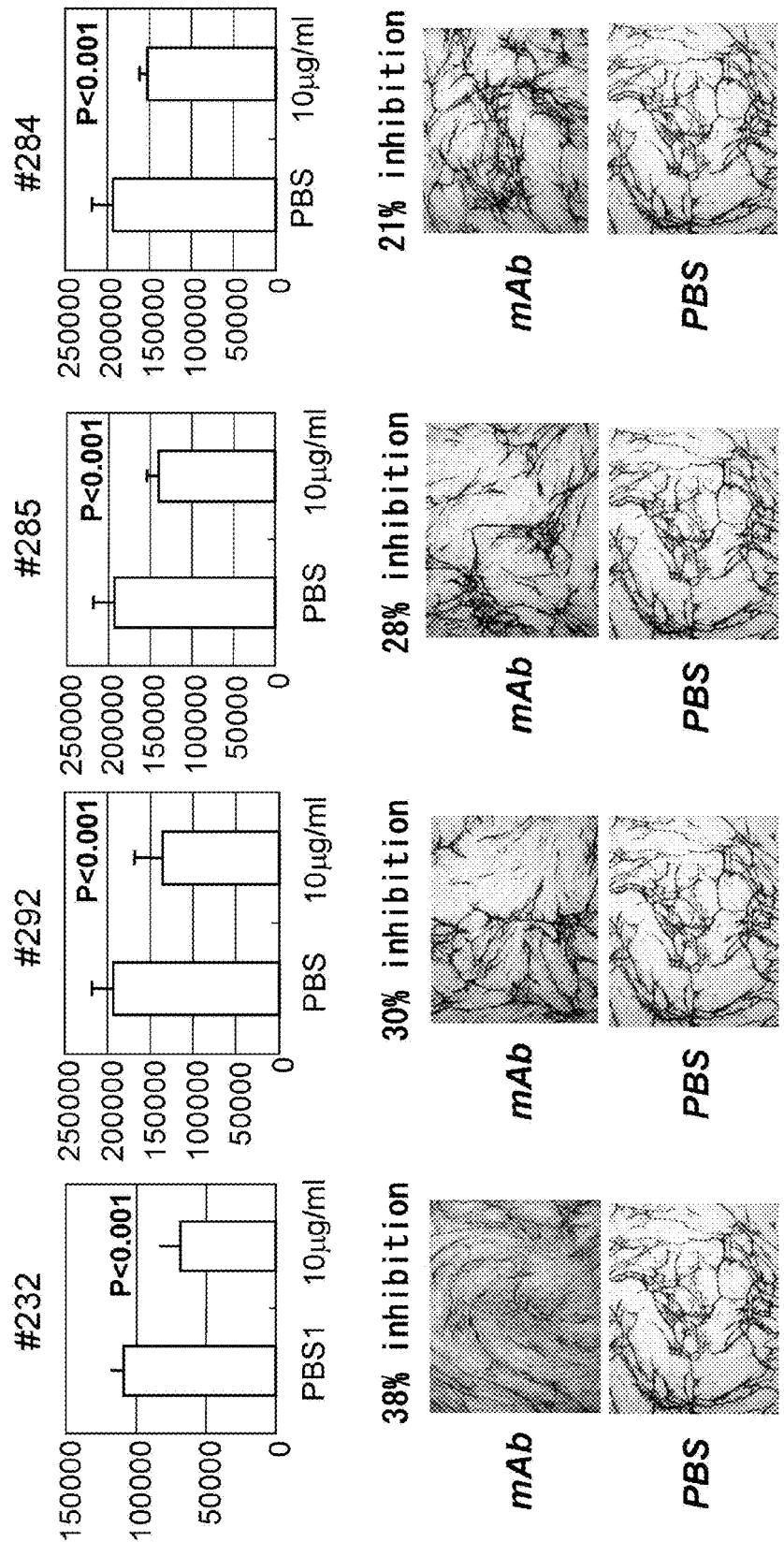
FIG. 4 is a drawing and photograph showing the activity of the anti-AXL monoclonal antibodies of the present invention (Ax232, Ax292, Ax285, and Ax284) in inhibiting in vitro angiogenesis. The antibodies were shown to have an inhibitory activity of in vitro angiogenesis.

The rate of the reduction in the area of the vessels that formed in a lumen in the wells to which was added anti-AXL antibody relative to the area of the vessels that formed in a lumen in the wells to which was added the negative control PBS(−) was used as the index of the inhibitory activities of the antibodies, and Ax232, Ax292, Ax285, and Ax284 displayed inhibitory activity (FIG. 4).

Example 6

Binding Activity of the Anti-AXL Antibody to Mouse AXL

After the extracellular domain of mouse AXL (hereinafter referred to as mAXL-ECD; R&D) was diluted with coating buffer (100 mM sodium bicarbonate buffer, pH 9.6) to 2 µg/mL, 100 µL was dispensed into a 96-well plate (Nunc-Immuno™ 96 MicroWell™ MaxiSorp™ plates; Nalge Nunc International). After the plate was placed in a refrigerator overnight, the antibody solution in the plate was removed, 200 µL/well of diluent buffer (BlockingOne; Nacalai Tesque) was dispensed, and then blocked for two hours at room temperature. After the removal of the diluent buffer, the anti-AXL antibody prepared above diluted to 3 µg/mL with diluent buffer was dispensed at 100 µL/well, and allowed to stand for 1.5 hours at room temperature. After the removal of the antibody solution, the wells were washed three times with tPBS (−). A labeled antibody cocktail containing alkaline-phosphatase-labeled goat anti-mouse IgG1 antibody, alkaline-phosphatase-labeled goat anti-mouse IgG2a antibody, and alkaline-phosphatase-labeled goat anti-mouse IgG2b antibody (SouthernBiotech) was prepared with final dilutions of each antibody of 1/2250:1/4000:1/4000, and was dispensed at 100 µL/well, and allowed to stand for one hour at room temperature. After the removal of the antibody solution, the wells were washed three times with tPBS(−). 100 µL/well of alkaline phosphatase chromogenic substrate solution (Blue-Phos Microwell Phosphatase Substrate System, Kirkegaad & Perry Laboratories) was dispensed, followed by color development at room temperature. The absorbance at 650 nm was then measured with a microplate reader (Emax, Molecular Devices).

Binding to mouse AXL was confirmed for Ax96, Ax119, Ax223, Ax225, and Ax284.

Example 7

In Vitro Cancer Cell Growth Inhibitory Activity of the Anti-AXL Antibody

Evaluation was performed using HCT-116 (CCL-247), Calu-1 (HTB-54), DU-145 (HTB-81), and T-47D (HTB-133) purchased from ATCC, and AsPC-1, MDA-MB-231, and PANC-1 purchased from Dainippon Sumitomo Pharma. The cells were maintained under the conditions recommended by the supplier of each cell. A dilution series was prepared of the anti-AXL antibody produced as described above with 10% FBS/RPMI1640, and 20 µL was dispensed into a 96-well plate (flat bottom). Each of the suspensions of HCT-116, Calu-1, DU145, T-47D, AsPC-1, MDA-MB-231, and PANC-1 cells were prepared at 2000, 3000, 2000, 5000, 3000, 5000, and 3,000 cells per well, respectively, and 180 µL of cell suspension was added to each well and then cultured in an incubator at 37° C. in 5% $CO_2$. Four days later, 10 µL of WST-8 (Cell Counting Kit-8, Dojindo Laboratories) was added to each well and the absorbance at 450 nm was measured with a microplate reader (Model 3550-UV, Bio-Rad), according to the protocol provided with the kit. The cell inhibitory activity (%) of the anti-AXL antibodies was calculated by assigning a value of 0% inhibition to the value measured when no test substance was included, and assigning a value of 100% inhibition to a value measured when no test substance or cells were included.

Ax51 demonstrated CGI activity of 30% or more against HCT116 cells.

TABLE 2

| | HCT116 | | | | |
|---|---|---|---|---|---|
| | 1st | | | 2nd | |
| | TOP | ⅓ | ⅑ | TOP | 1/10 |
| Ax51 | 31 | 11 | 10 | 12 | 15 |

Example 8

Measurement of Antitumor Effects of the Anti-AXL Antibody in a Mouse Model Grafted with Human Pancreatic Adenocarcinoma 1. Preparation of a Mouse Model Grafted with Human Pancreatic Adenocarcinoma The human pancreatic adenocarcinoma cell line PANC-1, purchased from Dainippon Pharmaceutical (currently Dainippon Sumitomo Pharma), was prepared at $5 \times 10^7$ cells/mL with HBSS. 200 µL of the cell suspension ($1 \times 10^7$ cells/mouse) was subcutaneously grafted into the inguinal region of a CAnN.Cg-Foxn1<nu>/CrlCrlj nu/nu (BALB-nu/nu) mouse purchased from Charles River Laboratories, Japan. The mouse was subjected to the experiment when the tumor volume had reached about 210 mm³.

2. Antibody Preparation and Administration

The antibodies of Table 1 were prepared at 2 mg/mL with PBS and administered twice a week for two weeks at 20 mg/kg into the peritoneal cavity of the mouse grafted with human pancreatic adenocarcinoma. As the negative control, PBS was administered in the same manner. Gemzar (Eli Lilly Japan) was prepared at 12 mg/mL with physiological saline as the positive control and administered intraperitoneally at 120 mg/kg twice a week for two weeks.

3. Evaluation of Antitumor Effects

Figure 5:
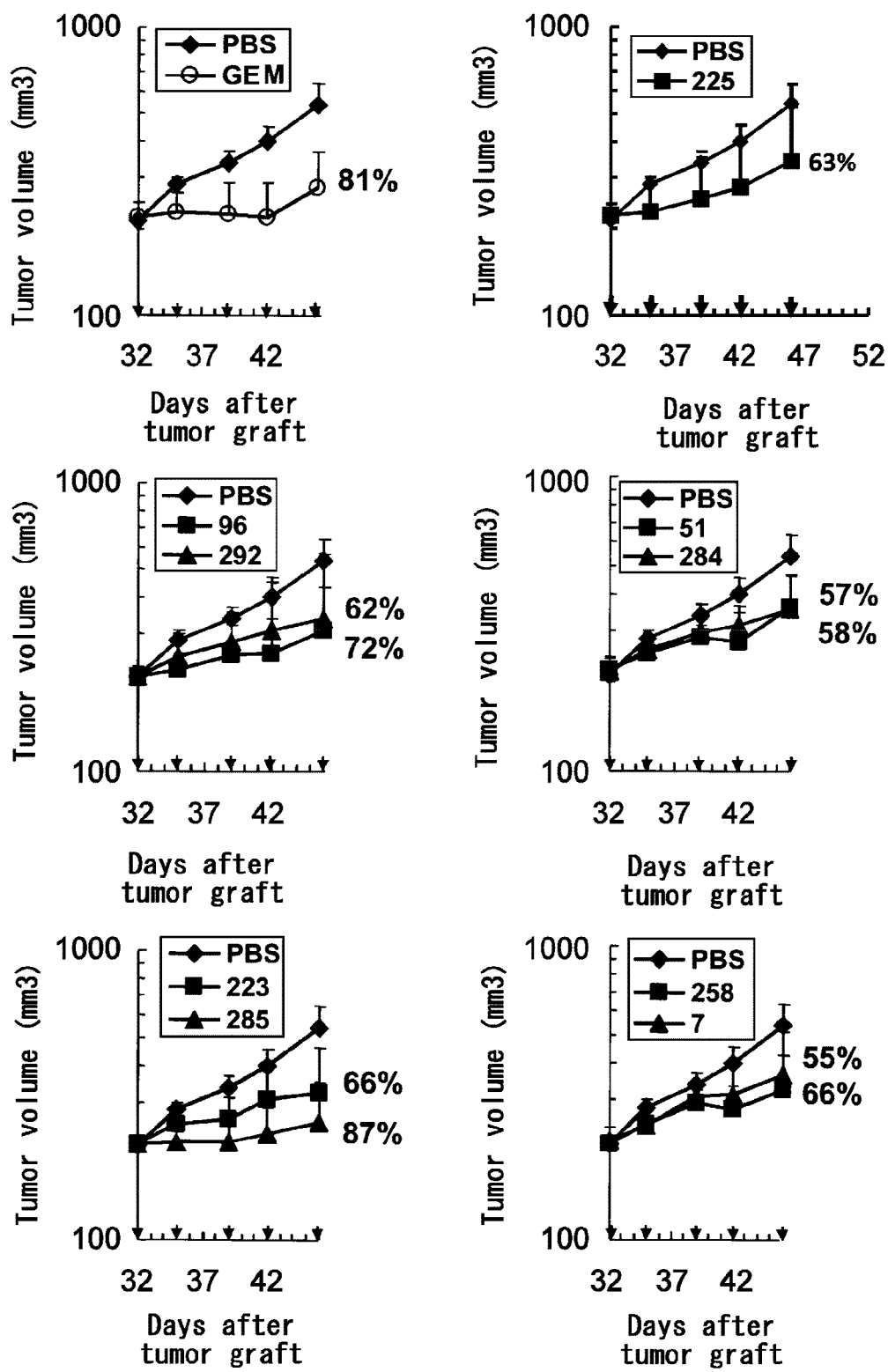
FIG. 5 is a drawing showing the antitumor effects of the anti-AXL monoclonal antibodies of the present invention (Ax223, Ax285, Ax96, Ax292, Ax258, Ax7, Ax51, Ax284, and Ax225) in a mouse xenograft model of human pancreatic adenocarcinoma.

The antitumor effects in a mouse model grafted with human pancreatic adenocarcinoma were calculated as tumor-growth-suppressive effects by comparing the tumor growth in the antibody-treated group with the tumor growth in the negative control group four days after the final administration (FIG. 5).

Tumor-growth-suppressive effect(%)=(1−amount of tumor growth in the antibody-treated group/ amount of tumor growth in the control group)× 100

4. Statistical Processing

Tumor volume was expressed as the mean±standard deviation. Statistical analysis consisted of a comparison between the control group and the treated group by the LSD method using the SAS Preclinical Package Ver. 5.0. Reliability of 95% (*: $p<0.05$) was determined to constitute significance.

5. Results

All of the antibodies inhibited tumor growth and demonstrated antitumor effects (FIG. 5).

Example 9

Measurement of Antitumor Effects of Anti-AXL Antibody on Mouse Model Transplanted with Human Pancreatic Adenocarcinoma (2)

1. Preparation of Mouse Model Grafted with Human Pancreatic Adenocarcinoma

Human pancreatic adenocarcinoma cell line PANC-1 purchased from Dainippon Pharmaceutical (currently Dainippon Sumitomo Pharma) was prepared to $5 \times 10^7$ cells/mL with HBSS. 200 µL of the cell suspension ($1 \times 10^7$ cells/mouse) were subcutaneously grafted to the inguinal regions of CAnN.Cg-Foxn1<nu>/CrlCrlj nu/nu (BALB-nu/nu) mice purchased from Japan Charles River. The mice were used in the experiment when the mean tumor volume reached about 270 mm$^3$.

2. Antibody Preparation and Administration

Anti-AXL antibody was prepared to 2 mg/mL with PBS and administered into the peritoneal cavity of the mice grafted with human pancreatic adenocarcinoma twice a week for two weeks at 20 mg/kg. PBS was administered in the same manner for use as a negative control. Gemzar (Eli Lilly Japan) was prepared to 12 mg/mL with physiological saline for use as a positive control and administered intraperitoneally twice a week for two weeks at 120 mg/kg.

3. Evaluation of Antitumor Effects

Antitumor effects in a mouse model grafted with human pancreatic adenocarcinoma were calculated as tumor growth suppressive effects by comparing with the amount of tumor growth of a negative control group four days after final administration.

Tumor growth suppressive effect(%)=(1−amount of tumor growth of the antibody-treated group/amount of tumor growth of the control group)×100

4. Results

The results for suppression of tumor growth are shown in FIG. 6. A tumor growth suppressive effect (%) of lower than 30% is indicated as "−", that of 30% or more is indicated as "+", and that of 60% or more is indicated as "++". The results for the assay of inhibition of ligand-dependent phosphorylation by antibody of Example 3 are also shown in FIG. 6.

Antibodies that bind to FND-1 demonstrated 60% or more of TGI activity even if administration was begun at the time when mean tumor volumes had reached about 270 mm$^3$. This finding that anti-AXL antibodies that bind to FND1 have such significant antitumor effects in vivo was determined for the first time in this study and was completely unexpected.

In addition, the existence of anti-AXL antibodies that bind to IgD2 that demonstrate phosphorylation inhibitory effect and in vivo antitumor effects as indicated in Examples 3, 8, and 9 was also discovered for the first time in this study and was also completely unexpected.

Example 10

Binding Activity to Human AXL-FND1 and Human AXL-IgD2

1. Binding Activity to Human AXL-FND1 and Human AXL-IgD2

The binding abilities of anti-AXL monoclonal antibody to AXL-fibronectin type 3 domain 1 (AXL-FND1) and AXL immunoglobulin family domain 2 (AXL-IgD2) were tested.

2. Preparation of Human Recombinant AXL-FND1 and Human Recombinant AXL-IgD2 Expression Vectors Human recombinant AXL-FND1 was prepared by amplifying by PCR a region equivalent to the 225th to 331st amino acids from full-length human AXL cDNA (O'Bryan, et al., Mol. Cell. Biol. (1991) 11, 5016-5031) (GenBank No. NM 021913), cloning the amplified products to pET-41a(+) (Novagen) to express fusion proteins with GST-tag, and constructing pET-AXL-FND1. Other domains were prepared by amplifying by PCR a region equivalent to the 137th to 224th amino acids, and cloning the amplified products to pET-41a (+) to express fusion proteins with GST tag. Each of the prepared vectors (5 µl) was transformed to DH5α (Toyobo Co., Ltd., Cat. No. DNA-903) by a heat shock method and then cultured in SOC medium. Colonies were selected after culturing overnight at 37° C. on an LB plate containing kanamycin.

3. Purification of Human Recombinant AXL-FND1 and Human Recombinant AXL-IgD2

Each of the produced colonies were precultured overnight at 37° C. in 20 mL of LB medium containing kanamycin and then transferred to 500 mL of medium. The each colony was cultured to an $A_{600}$ of 0.5±0.05 and IPTG was added to be a concentration of 0.5 mM. After culturing for one hour at 37° C., the bacterial cells were collected and suspended in Buffer A (50 mM Tris-HCl (pH 8.0), 1 mM EDTA, 0.5 mM PMSF, and 1 mM DTT). Freezing and thawing was repeated twice using liquid nitrogen. NP-40 was then added to 0.5% and the cells were homogenized with an ultrasonic homogenizer (30 seconds×5) and centrifuged for 30 minutes at 204,000×G, and then the supernatant was recovered.

Human recombinant AXL-FND1 was purified in the manner described below using the resulting supernatant. Solubilized *E. coli* supernatant was mixed with Glutathione Sepharose™ 4 Fast Flow (GE Healthcare) and stirred for one hour at 4° C. with a rotator. After centrifugation for five minutes at 500×G, the supernatant was discarded and the Glutathione Sepharose™ 4B was washed by adding Buffer A. This washing procedure was repeated three times. After transferring the human recombinant AXL-FND1 from the washed Glutathione Sepharose™ 4 Fast Flow to a mini-column, it was separated and eluted from the Glutathione Sepharose™ 4 Fast Flow with 50 mM Tris-HCl (pH 7.5) and 25 mM glutathione. Each of other AXL domains was expressed, separated, and eluted in the same manner.

4. Evaluation of Binding Activity of Anti-AXL Antibody to AXL-FND1 by Western Blotting The recombinant AXL-FND1 separated and eluted from the Glutathione Sepharose™ 4 Fast Flow, as well as AXL-IgD1, AXL-IgD2, AXL-FND2, AXL-IgD1+IgD2, AXL-IgD2+FND1, and AXL-FND1+FND2 were quantified using the BIO-RAD Dc Protein Assay. 1 µg each was mixed with NuPAGE® Sample Buffer (Invitrogen), and electrophoresed with NuPAGE® 10% Bis-TrisGel. The electrophoresed gel was transferred to an Immobilon™-FL (Millipore) PVDF membrane. The PVDF membrane containing the transferred protein was blocked with Odyssey® Blocking Buffer (LI-COR) and immersed in a primary antibody solution in which anti-AXL antibody was diluted to 5 µg/mL, and incubated overnight at 4° C. The PVDF membrane containing the transferred protein and immersed in the primary antibody solution was washed four times for five minutes each with 0.1% TBS-T (TBS (Tris-Buffered Saline (Takara)) containing 0.1% Tween-20). The PVDF membrane immersed in anti-AXL antibody was immersed in Alexa Fluor® 680 Goat Anti-mouse IgG (H+L) (Invitrogen) secondary antibody solution diluted to 80 ng/mL and incubated for one hour at room temperature. After washing the PVDF membrane immersed in the secondary antibody solution three times for five minutes each with 0.1% TBS-T, the membrane was washed for five minutes with TBS-T containing 0.01% SDS and then washed for five minutes with TBS. The binding of the washed PVDF membrane was then evaluated by scanning with the Odyssey® far infrared imaging system.

5. Results

The evaluation results are shown in FIG. 6.

Anti-AXL antibody produced by a hybridoma deposited under Accession No. FERM BP-10854 (Ax225) was demonstrated to recognize FND1 of AXL (FIG. 6). Anti-AXL antibody produced by a hybridoma deposited under Accession No. FERM BP-10857 (Ax284) was considered to recognize FND1 and IgD2 of AXL (FIG. 6). Anti-AXL antibody produced by a hybridoma deposited under Accession No. FERM BP-10850 (Ax7) and anti-AXL antibody produced by a hybridoma deposited under Accession No. FERM BP-10851 (Ax51) were demonstrated to recognize IgD2 of AXL (FIG. 6).

Example 11

Measurement of Antitumor Effects of Anti-AXL Antibody on Mouse Model Grafted with Human Breast Cancer 1. Preparation of Mouse Model Grafted with Human Breast Cancer Human breast cancer cell line MDA-MB-435S obtained from ATCC was prepared to $5\times10^7$ cells/mL with HBSS. 200 μL of the cell suspension ($1\times10^7$ cells/mouse) was subcutaneously grafted to the inguinal regions of CAnN.Cg-Foxn1<nu>/CrlCrlj nu/nu (BALB-nu/nu) mice purchased from Japan Charles River. The mice were used in the experiment when the tumor volume reached about 200 mm$^3$.

2. Antibody Preparation and Administration

Anti-AXL antibody was prepared to 2 mg/mL with PBS and administered into the peritoneal cavity of the mice grafted with human breast cancer twice a week for two weeks at 20 mg/kg. PBS was administered in the same manner for use as a negative control.

3. Evaluation of Antitumor Effects

Antitumor effects in a mouse model grafted with human breast cancer were calculated as tumor growth suppressive effects by comparing with the amount of tumor growth of a negative control group four days after final administration.

Tumor growth suppressive effect(%)=(1−amount of tumor growth of the antibody-treated group/ amount of tumor growth of the control group)× 100

4. Statistical Processing

Figure 7:
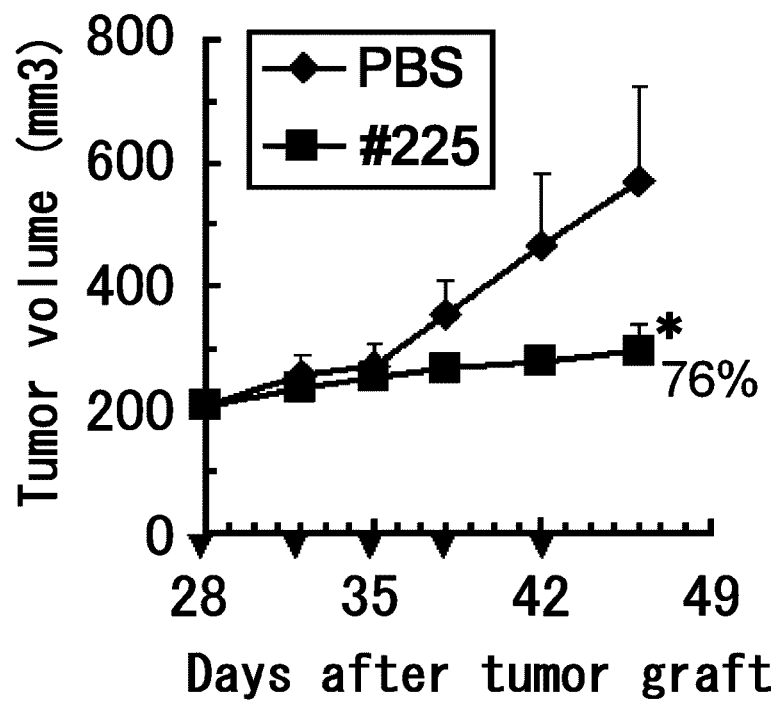
FIG. 7 is a drawing showing the antitumor effects of an anti-AXL monoclonal antibody (Ax225) of the present invention in a mouse xenograft model of human breast cancer.

Tumor volume was expressed as the mean±standard deviation. Statistical analysis consisted of a comparison between the control group and the treated group by the LSD method using the SAS Preclinical Package Ver. 5.0. Reliability of 95% (*: $p<0.05$) was determined to constitute significance 5. Results The used anti-AXL antibodies suppressed tumor growth and demonstrated antitumor effects (FIG. 7). Therefore, anti-AXL antibodies that bind to FND1 are expected to have antitumor effects against various tumors.

Example 12

Sequence Analysis of Antibody cDNA

1. Preparation of Chimeric Antibody-Expression Vectors

Total RNA was extracted from the cells of a hybridoma deposited under Accession No. FERM BP-10854 (Ax225) using the RNeasy Mini Kit (Qiagen), and cDNA was synthesized using the SMART RACE cDNA Amplification Kit (BD Biosciences). Antibody variable region gene was isolated by carrying out PCR with PrimeSTAR HS DNA Polymerase (Takara) using the following primers (H chain, MHCg1; L chain, MLCk) which were set for respective constant regions of antibody and 10× Universal Primer A Mix, provided with the SMART RACE cDNA Amplification Kit (BD Biosciences).

```
MHCg1:
5'-GGGCCAGTGGATAGACAGATG-3'     (SEQ ID NO. 1)

MLCk:
5'-GCTCACTGGATGGTGGGAAGATG-3'   (SEQ ID NO. 2)
```

The nucleotide sequence of each isolated DNA fragment was determined using the BigDye Terminator Cycle Sequencing Kit (Applied Biosystems) with the ABI PRISM 3730xL DNA Sequencer or ABI PRISM 3700 DNA Sequencer (Applied Biosystems) in accordance with the method described in the instructions provided.

2. Results

The heavy chain variable region of the amino acid sequence of the resulting Ax225 mouse antibody is shown in SEQ ID NO. 3, the CDR1 of that region is shown in SEQ ID NO. 4, CDR2 is shown in SEQ ID NO. 5, and CDR3 is shown in SEQ ID NO. 6. The light chain variable region of the amino acid sequence of the resulting Ax225 mouse antibody is shown in SEQ ID NO. 7, the CDR1 of that region is shown in SEQ ID NO. 8, CDR2 is shown in SEQ ID NO. 9, and CDR3 is shown in SEQ ID NO. 10.

INDUSTRIAL APPLICABILITY

The present inventors discovered for the first time that anti-AXL antibodies have an angiogenesis-suppressing effect and a cancer-suppressing effect. The anti-AXL antibody of the present invention is useful as an angiogenesis inhibitor and as a cell-growth suppressant. Using an antibody of the present invention, the phosphorylation of AXL can also be induced or inhibited. Moreover, using an antibody of the present invention, the expression level of AXL can be reduced.

The invention claimed is:

1. A monoclonal anti-AXL antibody according to any of the following (a) to (b):
   (a) a monoclonal antibody (Ax284) produced from a hybridoma deposited with the International Patent Organism Depositary (IPOD), National Institute of Advanced Industrial Science and Technology (AIST) and assigned Accession No. FERM BP-10857; and
   (b) a monoclonal antibody (Ax225) produced from a hybridoma deposited with the IPOD, AIST, and assigned Accession No. FERM BP-10854.

2. A monoclonal anti-AXL antibody that binds to the same epitope bound by either of
   (a) a monoclonal antibody (Ax284) produced from a hybridoma deposited with the IPOD, AIST, and assigned Accession No. FERM BP-10857; or
   (b) a monoclonal antibody (Ax225) produced from a hybridoma deposited with the IPOD, AIST, and assigned Accession No. FERM BP-10854.

3. A monoclonal anti-AXL antibody that comprises heavy chain CDR1, 2, and 3 amino acid sequences corresponding to SEQ ID NOs: 4, 5, and 6, respectively; and light chain CDR1, 2 and 3 amino acid sequences corresponding to SEQ ID NOs: 8, 9 and 10, respectively.

4. The anti-AXL antibody according to claim 3, wherein the antibody is a chimeric antibody.

5. The anti-AXL antibody according to claim 3, wherein the antibody is a humanized antibody.

6. An isolated hybridoma according to any of the following (a) to (b):
   (a) an isolated hybridoma deposited with IPOD, AIST, and assigned Accession No. FERM BP-10857 (Ax284); and
   (b) an isolated hybridoma deposited with the IPOD, AIST, and assigned Accession No. FERM BP-10854 (Ax225).

7. A monoclonal anti-AXL antibody that competes for binding to the same epitope bound by either of
   (a) a monoclonal antibody (Ax284) produced from a hybridoma deposited with the IPOD, AIST, and assigned Accession No. FERM BP-10857; or
   (b) a monoclonal antibody (Ax225) produced from a hybridoma deposited with the IPOD, AIST, and assigned Accession No. FERM BP-10854.

* * * * *